(12) United States Patent
Bukshpan et al.

(10) Patent No.: US 8,697,102 B2
(45) Date of Patent: Apr. 15, 2014

(54) COMPOSITIONS AND METHODS FOR CELL KILLING

(75) Inventors: Shmuel Bukshpan, Ramat Ha-Sharon (IL); Gleb Zilberstein, Rechovot (IL)

(73) Assignee: Oplon B.V., Delft (NL)

( * ) Notice: Subject to any disclaimer, the term of this patent is extended or adjusted under 35 U.S.C. 154(b) by 388 days.

(21) Appl. No.: 12/823,354

(22) Filed: Jun. 25, 2010

(65) Prior Publication Data

US 2010/0272768 A1 Oct. 28, 2010

Related U.S. Application Data

(63) Continuation-in-part of application No. 11/590,756, filed on Nov. 1, 2006, now Pat. No. 7,794,698.

(60) Provisional application No. 60/732,130, filed on Nov. 2, 2005.

(51) Int. Cl.
*A01N 25/34* (2006.01)
*A61K 31/74* (2006.01)

(52) U.S. Cl.
USPC .......... 424/404; 424/400; 424/78.1; 977/902; 977/778; 977/773

(58) Field of Classification Search
USPC .......... 424/16, 25–28, 78, 78.01, 78.08, 78.1, 424/78.18, 167.1, 400, 404; 977/773, 778, 977/902
See application file for complete search history.

(56) References Cited

U.S. PATENT DOCUMENTS

| | | | |
|---|---|---|---|
| 4,259,103 A * | 3/1981 | Malek et al. | 504/153 |
| 4,420,590 A | 12/1983 | Gartner | |
| 4,661,344 A | 4/1987 | Relenyi | |
| 5,561,167 A | 10/1996 | Matsumoto et al. | |
| 5,900,258 A | 5/1999 | Engler | |
| 6,022,553 A | 2/2000 | Anders | |
| 6,218,492 B1 | 4/2001 | Hill | |
| 6,290,946 B1 * | 9/2001 | Kurtz et al. | 424/78.08 |
| 6,316,015 B1 | 11/2001 | Rondelez | |
| 6,423,354 B1 | 7/2002 | Monte | |
| 6,514,517 B2 | 2/2003 | Jamiolkowski | |
| 6,517,826 B1 | 2/2003 | Kurtz et al. | |
| 2004/0146614 A1 | 7/2004 | Ottersbach | |
| 2004/0161473 A1 | 8/2004 | Joshi | |
| 2005/0003163 A1 | 1/2005 | Krishnan | |
| 2005/0244365 A1 | 11/2005 | Labib | |
| 2005/0249695 A1 | 11/2005 | Tiller | |
| 2005/0271780 A1 | 12/2005 | Schroeder et al. | |

FOREIGN PATENT DOCUMENTS

| | | | |
|---|---|---|---|
| EP | 0526541 A | 4/1990 | |
| EP | 0597695 A | 11/1993 | |
| WO | WO01/72859 A1 | 10/2001 | |
| WO | WO02/085542 | 10/2002 | |
| WO | WO02092650 A1 | 11/2002 | |
| WO | WO2006017245 A2 | 2/2006 | |
| WO | WO2007/052270 A1 | 5/2007 | |

OTHER PUBLICATIONS

Takeshi Endo et al., Polymeric Phosphonium Salts as a Novel Class of Cationic Biocides. IV. Synthesis and Antibacterial Activity of Polymers with Phoshonium Salts in the Main Chain, Journal of Polymer Science: Part A: Polymer Chemistry, vol. 31, 3031-3038 (1993).*
J Tiller (2001) Proc Natl Acad Sci 98(11): 5981-5985.
Y Endo (1987) Applied and Environmental Microbiol 53(9): 2050-2055.
S. Imazato (1995) J Dentistry 23(3): 177-181.
C Heitner-Wirguin (1996) 120: 1-33.
G Gerhardt (1984) Brain Research 290: 390-395.
EM Baskin (2006) Physical Biology 3: 101-106.
Boring et al. "Cancer Statistics 1993", CA: A Cancer Journal of Clinicians, 43: 7-26, 1993.
Endo et al., "Antimicrobial Activity of Tertiary Amine Covalently Bonded to A Polystyrene Fiber", Applied and Environmental Microbiology, 53(9): 2050-2055, 1987. P.2050, r-h col., Paragraph 2, P.2051, r-h Col., Last Line—P.2052, l-h Col., Paragraph 1.
Gerhardt et al. "Nafion-Coated Electrodes with High Selectivity for CNS Electrochemistry", Brain Research, 290(2): 390-395, 1984.
Heitner-Wirguin "Recent Advances in Perfluorinated Ionomer Membranes: Structure, Properties and Applications", Journal of Membrane Science, 120(1): 1-33, 1996.
Imazato et al. "Antibacterial Activity of MDPB Polymer Incorporated in Dental Resin", Journal of Densitry, 23(3): 177-181, 1995. P.178, r-h Col. Paragraph 2, Figs. 2-5.
Leighty "Solution for Pharmaceutical Processing: Pharmaceutical Facility Gets 'Green' Light with Gas Analysis Sampling System (GASS™)", Perma Pure LLC, www.permapure.com, 3P., 1995.
Perma Pure "Our Technology/Frequently Asked Questions/Products", Perma Pure LLC, 13 P., 2006.
Tiller et al. "Designing Surfaces that Kill Bacteria on Contact", Proc. Natl. Acad. Sci. USA 98(11): 5981-5985, 2001. P.598l, l-h Col. Paragraph 3, P.5982, r-h Col., Paragraph 2—P. 5984, r-h Col., Paragraph 2.

* cited by examiner

*Primary Examiner* — Michael G Hartley
*Assistant Examiner* — Jagadishwar Samala
(74) *Attorney, Agent, or Firm* — Pearl Cohen Zedek Latzer Baratz LLP

(57) ABSTRACT

A solid buffer including one or more ion exchange materials, wherein said solid buffer has a volumetric buffering capacity greater than about 20 mM $H^+$/(L.pH unit) and further wherein, when said material is in an environment capable of transporting $H^+$ ions, said solid buffer is adapted to cause the death of at least one target cell within or in contact with said environment. A selectively permeable barrier layer may be provided covering the solid buffer.

16 Claims, 9 Drawing Sheets

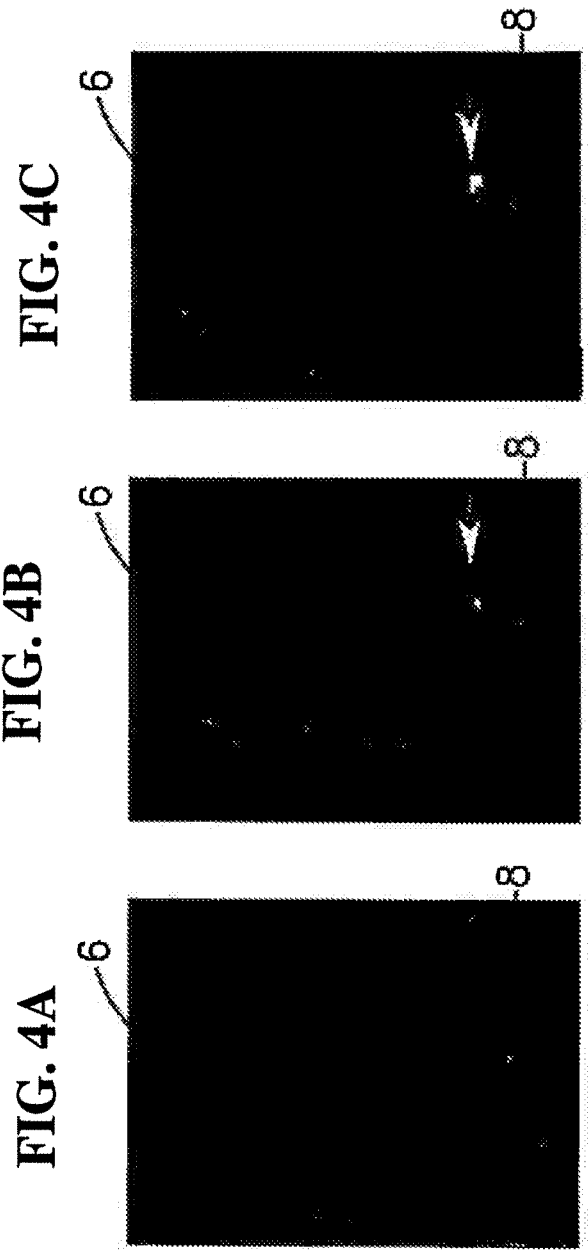

COMPOSITIONS AND METHODS FOR CELL KILLING

RELATED APPLICATION

This application is a Continuation-in-Part of U.S. patent application Ser. No. 11/590,756, filed 1 Nov., 2006, which claims the benefit of U.S. Provisional Patent Application No. 60/732,130, filed 2 Nov., 2005, the contents of both of which are hereby incorporated by reference in their entirety.

FIELD AND BACKGROUND OF THE INVENTION

The present invention relates to compositions and methods for killing cells based on the titration thereof with solid buffers.

Various forms of cellular material are known to be harmful and potentially lethal to man. For example, cancerous cells are the second leading cause of death in the United States, after heart disease (Boring et al., CA Cancer J. Clin. 43:7 (1993)). Cellular microorganisms are also responsible for a wide range of diseases. Cell killing and targeted cell killing (e.g., cancer) are highly investigated in the biotechnology industry.

A cancer is a malignant tumor of potentially unlimited growth. It is primarily the pathogenic replication (a loss of normal regulatory control) of various types of cells found in the human body. Initial treatment of the disease is often surgery, radiation treatment or the combination of these treatments, but locally recurrent and metastatic disease is frequent. Chemotherapeutic treatments for some cancers are available but these seldom induce long term regression. Hence, they are often not curative. Commonly, tumors and their metastases become refractory to chemotherapy, in an event known as the development of multidrug resistance. In many cases, tumors are inherently resistant to some classes of chemotherapeutic agents. In addition, such treatments threaten non-cancerous cells, are stressful to the human body, and produce many side effects. Improved agents that are capable of targeting cancerous cells are therefore needed.

Microorganisms can invade the host tissues and proliferate, causing severe disease symptoms. Pathogenic bacteria have been identified as a root cause of a variety of debilitating or fatal diseases including, for example, tuberculosis, cholera, whooping cough, plague, and the like. To treat such severe infections, drugs such as antibiotics are administered that kill the infectious agent. However, pathogenic bacteria commonly develop resistance to antibiotics and improved agents are needed to prevent the spread of infections due to such microorganisms.

One of the principal concerns with respect to products that are introduced into the body or provide a pathway into the body is bacterial infection. Avoiding such infections with implantable medical devices can be particularly problematic because bacteria can develop into biofilms, which protect the microbes from clearing by the subject's immune system. As these infections are difficult to treat with antibiotics, removal of the device is often necessitated, which is traumatic to the patient and increases the medical cost. Accordingly, for such medical apparatuses, the art has long sought means and methods of rendering those medical apparatuses and devices antibacterial and, hopefully, antimicrobial.

The general approach in the art has been that of coating the medical apparatuses, or a surface thereof, with a bactericide. However, since most bactericides are partly water soluble, or at least require sufficient solubilization for effective antibacterial action, simple coatings of the bactericides have been proven unreliable.

For this reason, the art has sought to incorporate the bactericides into the medical apparatus or at least provide a stabilized coating thereon.

Alternatively, materials can be impregnated with antimicrobial agents, such as antibiotics, quarternary ammonium compounds, silver ions, or iodine, which are gradually released into the surrounding solution over time and kill microorganisms there. Although these strategies have been verified in aqueous solutions containing bacteria, they would not be expected to be effective against airborne bacteria in the absence of a liquid medium; this is especially true for release-based materials, which are also liable to become impotent when the leaching antibacterial agent is exhausted.

Any agent used to impair biofilm formation in the medical environment must also be safe to the user. Certain biocidal agents, in quantities sufficient to interfere with biofilms, also can damage host tissues. Antibiotics introduced into local tissue areas can induce the formation of resistant organisms which can then form biofilm communities whose planktonic microorganisms would likewise be resistant to the particular antibiotics. Any anti-biofilm or antifouling agent must furthermore not interfere with the salubrious characteristics of a medical device. Certain materials are selected to have a particular type of operator manipulability, softness, water-tightness, tensile strength or compressive durability, characteristics that cannot be altered by an agent added for antimicrobial effects.

Food is also a source of bacterial infection and the preservation thereof is of utmost importance in order to keep food safe for consumption and inhibit or prevent nutrient deterioration or organoleptic changes, causing food to become less palatable and even toxic. Preservation of food products can be achieved using a variety of approaches. Physical manipulations of food products that have a preservative effect include, for example, freezing, refrigerating, cooking, retorting, pasteurizing, drying, vacuum packing and sealing in an oxygen-free package. Some of these approaches can be part of a food processing operation. Food processing steps preferably are selected to strike a balance between obtaining a microbially-safe food product, while producing a food product with desirable qualities.

With the increasing use of polymeric materials for construction of medical apparatuses and packaging and handling of food products, utilizing an antimicrobial polymer has become ever more desirable. Although, antimicrobial polymers exist in the art, there is still a need for an improved antimicrobial polymer coating that may be easily and cheaply applied to a substrate to provide an article which has excellent antimicrobial properties and which retains its antimicrobial properties in a permanent and non-leachable fashion when in contact with cellular material for prolonged periods.

U.S. Pat. Appl No. 20050271780 teaches a bactericidal polymer matrix being bound to an ion exchange material such as a quaternary ammonium salt for use in food preservation. This polymer matrix kills bacteria by virtue of incorporating therein of a bactericidal agent (e.g. the quaternary ammonium salt). The positive charge of the agent merely aids in electrostatic attraction between itself and the negatively charged cell walls. In addition, the above described application does not teach use of solid buffers having a buffering capacity throughout their entire body.

U.S. Pat. Appl. No. 20050249695 teaches immobilization of antimicrobial molecules such as quarternary ammonium or phosphonium salts (cationic, positively charged entities)

covalently bound onto a solid surface to render the surface bactericidal. The polymers described herein are attached to a solid surface by virtue of amino groups attached thereto and as such the polymer is only capable of forming a monolayer on the solid surface.

U.S. Pat. Appl. No. 20050003163 teaches substrates having antimicrobial and/or antistatic properties. Such properties are imparted by applying a coating or film formed from a cationically-charged polymer composition.

The activity of the polymers as described in U.S. Pat. Appl. Nos. 20050271780, 20050249695 and 20050003163 relies on the direct contact of the bactericidal materials with the cellular membrane. The level of toxicity is strongly dependent on the surface concentration of the bactericidal entities. This requirement presents a strong limitation since the exposed cationic materials can be saturated very fast in ion exchange reactions.

In addition, none of the above described U.S. patent applications teach killing eukaryotic cells. Nor do they teach the in vivo use of polymers as cytotoxic agents against either eukaryotic or prokaryotic cell types. Furthermore, none of the above mentioned U.S. patent applications teach configuration of the polymers to selectively kill certain cell types.

There thus remains a need for and it would be highly advantageous to have agents capable of cytotoxic action both against eukaryotic and prokaryotic cells.

SUMMARY OF THE INVENTION

According to one aspect of the present invention there is provided a method of generating a change in a cellular process of a target cell of a multicellular organism, the method comprising contacting the target cell with a solid buffer, so as to alter an intracellular pH value in at least a portion of the cell, thereby generating the change in a cellular process of a target cell of a multicellular organism.

According to another aspect of the present invention there is provided a method of killing a target cell of a multicellular organism comprising contacting the target cell with a solid buffer, so as to alter an intracellular pH value in at least a portion of the cell, thereby killing the target cell.

According to yet another aspect of the present invention there is provided a method of generating a change in a cellular process of a target cell, the method comprising contacting the target cell with a solid buffer, the solid buffer being anionic, so as to alter an intracellular pH value in at least a portion of the cell, thereby generating the change in a cellular process of a target cell.

According to still another aspect of the present invention there is provided a method of generating a change in a cellular process of a target cell, the method comprising contacting the target cell with a solid buffer, wherein the solid buffer comprises a buffering layer and a water permeable layer being disposed on an external surface of the buffering layer, so as to alter an intracellular pH value in at least a portion of the cell, thereby killing the cell.

According to an additional aspect of the present invention there is provided a method of killing a cell comprising contacting the cell with a solid buffer, the solid buffer comprising a volumetric buffering capacity greater than 50 mM $H^+$/l.pH, and a pH either greater than pH 8, or less than pH 4.5, thereby killing the cell.

According to still an additional aspect of the present invention there is provided a method of selecting a solid buffer capable of killing a cell, the method comprising selecting a solid buffer having a volumetric buffering capacity greater than 50 mM H/l.pH, and a pH greater than pH 8 or a pH less than pH 4.5, the solid buffer being capable of killing the cell.

According to still an additional aspect of the present invention there is provided a method of killing a sub-population of cells of interest, the method comprising contacting a sample which comprises the sub-population of cells of interest with a solid buffer having a volumetric buffering capacity and a pH selected suitable for specifically killing the sub-population of cells of interest, thereby killing the sub-population of cells of interest.

According to yet an additional aspect of the present invention there is provided an article of manufacture comprising:
(i) a support; and
(ii) a solid buffer layer being attached to at least part of a surface of the support, the solid buffer comprises a buffering layer and an ion permeable layer being disposed on an external surface of the buffering layer.

According to still an additional aspect of the present invention there is provided an article of manufacture comprising:
(i) a support; and
(ii) a solid buffer layer being attached to at least part of a surface of the support, the solid buffer being anionic.

According to still an additional aspect of the present invention there is provided a use of a solid buffer for the manufacture of a medicament for treating a medical condition associated with a pathological cell population.

According to a further aspect of the present invention there is provided a pharmaceutical composition comprising as an active ingredient a solid buffer and a pharmaceutically acceptable carrier or diluent.

According to yet a further aspect of the present invention there is provided an assay for selecting an optimal solid buffer for killing a cell of interest, the assay comprising:
(i) contacting a plurality of cells with a plurality of solid buffer agents;
(ii) identifying a solid buffer agent of the plurality of solid buffer agents capable of killing a cell of the plurality of cells, the solid buffer agent being optimized for killing the cell of interest.

According to yet a further aspect of the present invention there is provided a method of treating a medical condition associated with a pathological cell population, the method comprising administering into a subject in need thereof a therapeutically effective amount of a solid buffer so as to alter at least a portion of an intracellular pH value of the pathological cell population, thereby treating the medical condition associated with the pathological cell population.

According to further features in preferred embodiments of the invention described below, generating the change results in death of the cell.

According to still further features in the described preferred embodiments the multicellular organism is a higher plant.

According to still further features in the described preferred embodiments the multicellular organism is a mammal.

According to still further features in the described preferred embodiments the contacting is effected in vivo.

According to still further features in the described preferred embodiments the contacting is effected ex vivo.

According to still further features in the described preferred embodiments the contacting is effected in vitro.

According to still further features in the described preferred embodiments the solid buffer comprises a pH gradient along at least a portion thereof.

According to still further features in the described preferred embodiments the solid buffer is internalized by the target cell.

According to still further features in the described preferred embodiments the solid buffer is attached to an affinity moiety.

According to still further features in the described preferred embodiments the affinity moiety is selected from the group consisting of an antibody, a receptor ligand and a carbohydrate.

According to still further features in the described preferred embodiments the solid buffer is at least partially covered by a selective barrier.

According to still further features in the described preferred embodiments the selective barrier is a mechanical barrier.

According to still further features in the described preferred embodiments the solid buffer comprises a buffering layer and a water permeable layer being disposed on an external surface of the buffering layer.

According to still further features in the described preferred embodiments the water permeable layer is an open pore polymer.

According to still further features in the described preferred embodiments the open pore polymer is selected from the group consisting of PVOH, cellulose and polyurethane.

According to still further features in the described preferred embodiments the solid buffer is formulated in particles.

According to still further features in the described preferred embodiments the solid buffer is formulated as a spray.

According to still further features in the described preferred embodiments the solid buffer is encapsulated within the particles.

According to still further features in the described preferred embodiments the solid buffer is attached on the particle surface.

According to still further features in the described preferred embodiments the particles are selected from the group consisting of polymeric particles, microcapsules liposomes, microspheres, microemulsions, nanoparticles, nanocapsules and nanospheres.

According to still further features in the described preferred embodiments the solid buffer is an anionic, ion exchange material incorporated in a water permeable polymer matrix.

According to still further features in the described preferred embodiments the solid buffer is a cationic, ion exchange material incorporated in a water permeable polymer matrix.

According to still further features in the described preferred embodiments the solid buffer comprises a cationic ion exchange material and an anionic ion exchange material incorporated in a water permeable polymer matrix.

According to still further features in the described preferred embodiments the cationic ion exchange material is selected from the group consisting of sulfonic acid and derivatives thereof, phosphonic acid and derivatives thereof, carboxylic acid and derivatives thereof, phosphinic acid and derivatives thereof, phenols and derivatives thereof, arsonic acid and derivatives thereof and selenic acid and derivatives thereof.

According to still further features in the described preferred embodiments the anionic ion exchange material is selected from the group consisting of a quaternary amine, a tertiary amine, a secondary amine and a primary amine.

According to still further features in the described preferred embodiments the solid buffer is a polymer.

According to still further features in the described preferred embodiments the solid buffer comprises an intrinsically ion conducting matrix.

According to still further features in the described preferred embodiments the solid buffer is an ionomer.

According to still further features in the described preferred embodiments the ionomer is sulfonated tertafluorethylene copolymer (Nafion) and derivatives thereof.

According to still further features in the described preferred embodiments the solid buffer comprises a volumetric buffering capacity between about 20-100 mMH$^+$/1 pH.

According to still further features in the described preferred embodiments the solid buffer comprises a pH greater than pH 8.

According to still further features in the described preferred embodiments the solid buffer comprises a pH less than pH 4.5.

According to still further features in the described preferred embodiments the cell is a diseased cell.

According to still further features in the described preferred embodiments the solid buffer is attached to at least part of a surface of a support.

According to still further features in the described preferred embodiments the sample comprises at least a second sub-population of cells, wherein the sub-population of cells of interest and the second sub-population of cells exhibit different plasma buffering capacities.

According to still further features in the described preferred embodiments the treating is effected ex-vivo.

According to still further features in the described preferred embodiments the treating is effected in-vivo.

According to still further features in the described preferred embodiments the article of manufacture forms at least a part of a packaging material, a metical device, a fabric, a scaffold, a filter, or a bactericidal device.

It is an object of the present invention to provide a solid buffer comprising one or more ion exchange materials, wherein said solid buffer has a volumetric buffering capacity greater than about 20 mM H$^+$/(L.pH unit) and further wherein, when said material is in an environment capable of transporting H$^+$ ions, said solid buffer is adapted to cause the death of at least one target cell within or in contact with said environment.

It is a further object of the present invention to provide the aforementioned solid buffer wherein said target cell is a bacterial cell, a fungal cell or a yeast cell.

It is a further object of the present invention to provide the solid buffer wherein said target cell is a bacterial cell.

It is a further object of the present invention to provide the solid buffer wherein said solid buffer is adapted to kill said target cell without inserting any of its structure into the membrane of said target cell.

It is a further object of the present invention to provide the solid buffer characterized by one or more functional groups selected from the group consisting of sulfonic acid, phosphonic acid, quaternary amine, tertiary amine, and derivatives thereof.

It is a further object of the present invention to provide the solid buffer characterized by one or more functional groups selected from the group consisting of carboxylic acid and derivatives thereof, phosphinic acid and derivatives thereof, phenol and derivatives thereof, arsonic acid and derivatives thereof, selenic acid and derivatives thereof, secondary amine and derivatives thereof, and primary amine and derivatives thereof. It is a further object of the present invention to provide the solid buffer wherein said solid buffer comprises sulfonated tetrafluoroethylene copolymer and/or derivatives thereof.

It is a further object of the present invention to provide the solid buffer wherein the solid buffer is selected from the group consisting of polyacrylamide-immobilines, agarose-immobilines, poly(diethylaminoethyl acrylate), cationic polyurethane, cationic sub micron silica, and ion exchange beads.

It is a further object of the present invention to provide the solid buffer wherein the volumetric buffering capacity is at least about 50 mM $H^+$/(L.pH unit).

It is a further object of the present invention to provide the solid buffer wherein the volumetric buffering capacity is at least about 100 mM $H^+$/(L.pH unit).

It is a further object of the present invention to provide the solid buffer, further characterized by an $H^+$ concentration of greater than about $3.2 \times 10^{-5}$ M or less than about $10^{-8}$ M.

It is a further object of the present invention to provide the The solid buffer of claim 1 wherein the solid buffer comprises a pH gradient along at least a portion thereof.

It is a further object of the present invention to provide the solid buffer wherein the solid buffer comprises a plurality of regions of differing pH.

It is a further object of the present invention to provide the solid buffer wherein the ion exchange material is a polymer.

It is a further object of the present invention to provide the solid buffer wherein the ion exchange material comprises cationic silica.

It is a further object of the present invention to provide the solid buffer wherein the solid buffer comprises one or more of an ion exchange bead, a polymer-coated ion exchange bead, and an ion exchange material incorporated in a matrix.

It is a further object of the present invention to provide the solid buffer wherein the solid buffer comprises one or more of a water soluble polymer, a water permeable polymer, an intrinsically ion-conducting polymer, an ion permeable polymer, and a water-permeable ceramic.

It is a further object of the present invention to provide the solid buffer wherein the solid buffer comprises at least a portion of a coating or a component of a medical device, a wound dressing, sutures, cloth, fabric and a wound ointment.

It is a further object of the present invention to provide the solid buffer wherein the solid buffer is in the form of a shaped article, a coating, a spray, a film, a laminate on a film, a film in a laminate, sheets, beads, beads incorporated in fabric, particles, microparticles, microcapsules, microemulsions or nanoparticles.

It is a further object of the present invention to provide the solid buffer, covered by a barrier layer, said barrier layer characterized as being selectively permeable to water.

It is a further object of the present invention to provide the solid buffer, covered by a barrier layer, said barrier layer characterized as being permeable to a preselected target cell but not to preselected non-target cells.

It is a further object of the present invention to provide the composition of matter comprising (a) a solid buffer comprising one or more ion exchange materials, said solid buffer characterized by a volumetric buffering capacity of greater than about 20 mM $H^+$/(L.pH unit); and (b) a selectively permeable barrier layer covering said solid buffer; said composition of matter characterized by being adapted to kill at least one target cell located in an environment capable of transporting $H^+$ ions and in contact with said composition of matter.

It is a further object of the present invention to provide the aforementioned composition of matter wherein said selectively permeable barrier layer is selectively permeable to water.

It is a further object of the present invention to provide the aforementioned composition of matter wherein said selectively permeable barrier layer is selectively permeable to a preselected target cell but not to preselected non-target cells.

It is a further object of the present invention to provide the aforementioned composition of matter wherein said barrier layer comprises at least one form selected from the group consisting of coating, film, and membrane.

It is a further object of the present invention to provide the aforementioned composition of matter, wherein said barrier layer is selected from the group consisting of an open pore polymer, an open pore ceramic and an open pore gel.

It is a further object of the present invention to provide the aforementioned composition of matter wherein said barrier layer is an open pore polymer selected from the group consisting of one or more of polyvinyl alcohol, cellulose, ethyl cellulose, cellulose acetate, polyacrylamide and polyurethane.

It is a further object of the present invention to provide the aforementioned composition of matter wherein said target cell is a bacterial cell, a fungal cell or a yeast cell.

It is a further object of the present invention to provide the aforementioned composition of matter wherein the non-target cells are chosen from the group consisting of (a) mammalian cells, (b) plant cells, and (c) any combination of the above.

It is a further object of the present invention to provide the composition of matter wherein said target cell is a bacterium.

It is a further object of the present invention to provide the composition of matter wherein said solid buffer is further characterized by having an $H^+$ concentration of greater than about $3.2 \times 10^{-5}$ M or less than about $10^{-8}$ M.

It is a further object of the present invention to provide the composition of matter wherein said solid buffer has a volumetric buffering capacity of at least about 50 mM $H^+$/(L.pH unit).

It is a further object of the present invention to provide the composition of matter wherein said solid buffer has a volumetric buffering capacity of at least about 100 mM $H^+$/(L.pH unit).

It is a further object of the present invention to provide the composition of matter wherein said solid buffer comprises one or more functional groups selected from the group consisting of sulfonic acid, phosphonic acid, quaternary amine, tertiary amine, and derivatives thereof.

It is a further object of the present invention to provide the composition of matter wherein said solid buffer comprises one or more functional groups selected from the group consisting of carboxylic acid and derivatives thereof, phosphinic acid and derivatives thereof, phenol and derivatives thereof, arsonic acid and derivatives thereof, selenic acid and derivatives thereof, secondary amine and derivatives thereof, and primary amine and derivatives thereof.

It is a further object of the present invention to provide the composition of matter wherein said solid buffer comprises at least one substance selected from the group consisting of sulfonated tetrafluoroethylene copolymer and derivatives of sulfonated tetrafluoroethylene.

It is a further object of the present invention to provide the composition of matter wherein said solid buffer is selected from the group consisting of polyacrylamide-immobilines, agarose-immobilines, poly(diethylaminoethyl acrylate), cationic polyurethane, cationic sub micron silica, and ion exchange beads.

It is a further object of the present invention to provide the composition of matter wherein said solid buffer is adapted to kill living target cells without inserting any of its structure into an outer cell membrane of the target cell.

It is a further object of the present invention to provide the composition of matter wherein said barrier layer is adapted to prevent ions larger than $H^+$ and $OH^-$ from neutralizing said solid buffer.

It is a further object of the present invention to provide the composition of matter wherein said target cell is chosen from the group consisting of bacterial cells, fungal cells, and yeast cells.

It is a further object of the present invention to provide the composition of matter wherein said target cell is a bacterial cell.

It is a further object of the present invention to provide the composition of matter wherein said solid buffer kills target cells without inserting any of its structure into the outer membrane of said target cells.

It is a further object of the present invention to disclose a method of generating a change in a cellular process of a target eukaryotic cell of a multicellular organism, said method comprising contacting said target cell with a solid buffer so as to alter an intracellular pH value in at least a portion of said target cell, thereby generating said change in a cellular process of a target cell of a multicellular organism.

It is a further object of the present invention to disclose the abovementioned method of generating a change in a cellular process of a target eukaryotic cell, said method comprising contacting the target cell with a solid buffer so as to alter an intracellular pH value in at least a portion of said target cell, thereby generating said change in a cellular process of a target cell.

It is a further object of the present invention to disclose the abovementioned method wherein said eukaryotic target cell is a yeast cell.

It is a further object of the present invention to disclose the abovementioned method wherein said contacting is effected in vivo.

It is a further object of the present invention to disclose the abovementioned method wherein said contacting is effected ex vivo.

It is a further object of the present invention to disclose the abovementioned method wherein said contacting is effected in vitro.

It is a further object of the present invention to disclose the abovementioned method wherein generating said change results in death of said target cell.

It is a further object of the present invention to disclose the abovementioned method wherein said solid buffer comprises an anionic ion exchange material incorporated in a water permeable polymer matrix.

It is a further object of the present invention to disclose the abovementioned method wherein said solid buffer comprises a cationic ion exchange material incorporated in a water permeable polymer matrix.

It is a further object of the present invention to disclose the abovementioned method wherein said solid buffer comprises a polymer.

It is a further object of the present invention to disclose the abovementioned method wherein said solid buffer comprises an ionomer.

It is a further object of the present invention to disclose the abovementioned method wherein said solid buffer comprises a sulfonated tetrafluoroethylene copolymer or derivative thereof.

It is a further object of the present invention to disclose the abovementioned method wherein said solid buffer comprises an intrinsically ion conducting matrix.

It is a further object of the present invention to disclose the abovementioned method wherein said solid buffer is attached to an affinity moiety.

It is a further object of the present invention to disclose the abovementioned method wherein said solid buffer is at least partially covered by a selective barrier.

It is a further object of the present invention to disclose the abovementioned method wherein said solid buffer comprises a volumetric buffering capacity greater than about 20 mM $H^+$/ml/pH.

It is a further object of the present invention to disclose the abovementioned method wherein said solid buffer comprises a pH greater than pH 8.

It is a further object of the present invention to disclose the abovementioned method wherein said solid buffer comprises a pH less than pH 4.5.

It is a further object of the present invention to disclose the abovementioned method wherein said solid buffer is attached to at least part of a surface of a support.

It is a further object of the present invention to disclose the abovementioned method wherein said solid buffer comprises a buffering layer and a water permeable layer disposed on an external surface of said buffering layer.

It is a further object of the present invention to disclose the abovementioned method wherein said water permeable layer is an open pore polymer.

It is a further object of the present invention to disclose a method of treating a medical condition associated with a pathological cell population, said method comprising administering into a subject in need thereof a therapeutically effective amount of a solid buffer so as to alter at least a portion of an intracellular pH value of the pathological cell population, thereby treating the medical condition associated with the pathological cell population.

It is a further object of the present invention to disclose the abovementioned method further comprising the additional step of administering a therapeutically effective amount of said solid buffer to a subject suffering from a medical condition characterized by a pathological cell population, wherein said method provides a treatment for said medical condition.

It is a further object of the present invention to disclose the abovementioned method wherein said solid buffer is internalized by said target cell.

It is a further object of the present invention to disclose a pharmaceutical composition comprising as active ingredient a solid buffer and a pharmaceutically acceptable carrier or diluent.

It is a further object of the present invention to disclose the above-mentioned pharmaceutical composition wherein said solid buffer is formulated in particles.

It is a further object of the present invention to disclose an article of manufacture comprising (a) a support and (b) a solid buffer layer being attached to at least part of a surface of said support, said solid buffer comprises a buffering layer and an ion permeable layer being disposed on an external surface of said buffering layer.

It is a further object of the present invention to disclose an article of manufacture comprising (a) a support and (b) a solid buffer layer being attached to at least part of a surface of said support, said solid buffer being anionic.

The present invention successfully addresses the shortcomings of the presently known configurations by providing novel methods of affecting a cellular change by contacting cells with a solid buffer.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 3A is a top view of the experimental chamber immediately after the mixture of myoglobin and phycocyanin was placed in the middle compartment 2. FIG. 3B is a top view of the same experimental chamber photographed seven days following disposition of the mixture of myoglobin and phycocyanin in the middle compartment 2.

FIGS. 4A-C are composite photomicrographs illustrating the temporal variation of GFP distribution in a cell following attachment of the cell to a pH modifying bead. FIG. 4A represents a cell (8) attached to a bead (6) at time zero (defined as the time of attachment of the cell to the bead). FIG. 4B represents the cell (8) attached to the bead (6), as photographed ten minutes after the leftmost photograph was taken. FIG. 4C represents the cell (8) attached to the bead (6), as photographed thirty (30) minutes after the leftmost photograph was taken. The fluorescing point labeled by the thick white arrows, represents the fluorescence of GFP that migrated and accumulated at the point of contact between the bead 6 and the cell 8.

FIG. 6A illustrates Jurkat cells on a non-Nafion surface. FIG. 6B illustrates Jurkat cells on a Nafion surface.

FIG. 8A illustrates control Jurkat cells (with no exposure to bioactive film) after 1 minute. FIG. 8B illustrates Jurkat cells with BIOACT 13 film added after 1 minute. FIG. 8C illustrates control Jurkat cells (with no exposure to bioactive film) after 10 minutes. FIG. 8D illustrates Jurkat cells with BIOACT 13 film added after 10 minutes.

FIG. 9A is a photograph of a necrotic tissue prior to the administration of the ion exchange resin beads. FIG. 9B is a photograph of the same tissue following a two day application of the ion exchange beads. FIG. 9C is a photograph of the fabric to which the ion exchange beads were applied.

DESCRIPTION OF THE PREFERRED EMBODIMENTS

Figure 1A:
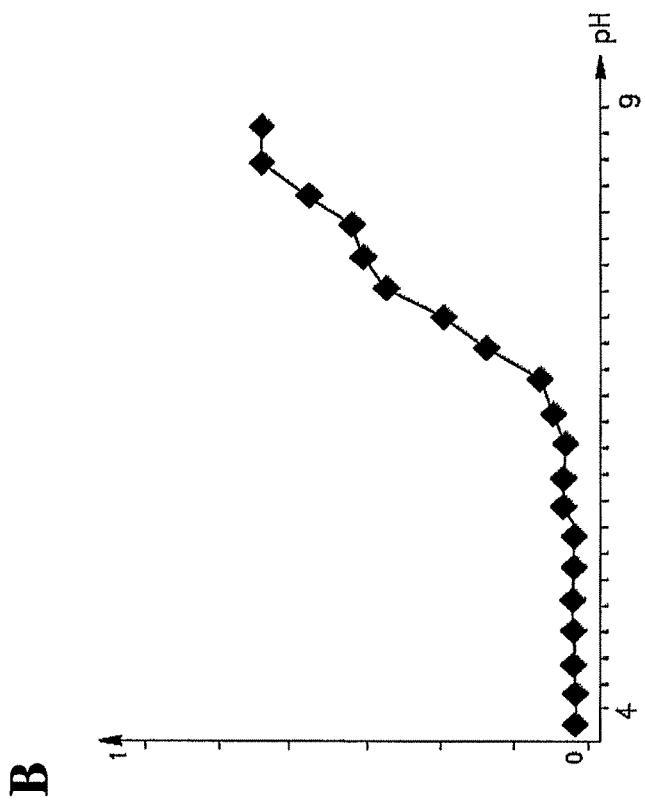
FIGS. 1A-B are graphs illustrating the spatial distribution of the native and urea denatured forms of the protein phycocyanin in strips containing polyacrylamide based gels having a pH gradient. The graph of FIG. 1A represents the results of the scan for native (non-denatured) phycocyanin. The graph of FIG. 1B represents the results of the scan for 8M Urea denatured phycocyanin. The vertical axes represent the Absorbance in O.D. units and the horizontal axes represent the position on the scanned gel strip expressed in pH units.

The present invention is of methods of affecting cellular processes using solid buffers. Specifically, the present invention may be exploited for a myriad of applications ranging from the killing of diseased cells in the body such as cancerous cells, to the killing of harmful prokaryotic cells in the environment.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

This invention is the result of a serendipitous and unexpected finding by the present inventors. They demonstrated that biomolecules (e.g. proteins) typically comprise a pH characteristic which determines their spatial distribution along a pH gradient (See Example 1). Further experimentation provided evidence that this redistribution can also occur across a biological membrane (See Example 3, FIGS. 4A-C).

Whilst conceiving the present invention, the present inventors uncovered that processes inside the cell may be manipulated by changing the extracellular pH of a solid buffer in contact therewith. Accordingly, the present inventors have shown that disruption of cellular pH homeostasis may be effected by contacting cells with a solid buffer comprising a pH which is different from the pH of the intracellular components. The contact results in the titration of the intracellular pH in the cytoplasm and generally leads to an alteration in a cellular process. Cell death may be effected when the pH of the buffering material is beyond the viability range of pH for a specific cell.

U.S. Pat. Appl. Nos. 20050271780, 20050249695 and 20050003163 teach bactericidal polymers. The polymers as taught therein rely on the direct contact of the polymer with the cellular membrane since the bactericidal activity originates from inclusion of cationic molecules, either immobilized on surfaces of, or incorporated in polymeric structures. The level of toxicity is strongly dependent on the surface concentration of the bactericidal entities. This requirement presents a strong limitation since the exposed cationic materials can be saturated very fast in ion exchange reactions.

The solid buffers taught within are not restricted to cationic polymers, but anionic buffers as well, since the novel mechanism of the present invention does not rely on the penetration of cationic groups to disrupt the cell membrane, but relies on an overall bulk buffering effect. The solid buffers taught herein are not restricted by the surface concentration of a bactericidal entity, since the cytotoxic activity thereof originates from their bulk properties and not just surface properties.

Whilst reducing the present invention to practice, the present inventors showed that solid buffers may exert a cytotoxic effect on all cell types, such as for example yeast cells (Example 4, Table 2), mammalian Jurkat cells (Example 5, Table 3) bacterial cells (Example 11, Table 5) and fungal cells (Example 12).

The present inventors further demonstrated that the rate of cell mortality may be controlled by the choice of the pH value of the solid buffer in contact with the cells, such that the rate of cell death can be fine tuned by suitably modifying the pH values of the solid buffer contacting the cells (See e.g., Example 4, Table 2).

In addition, the present inventors showed that pH-induced cytotoxicity requires direct contact of the cell with the solid buffer. Accordingly, physical barriers of a particular pore size may be attached to the solid buffer, such that pH homeostasis is disrupted (altered) for cells of a particular size only. In this fashion, cells of particular dimensions may be targeted leaving other cells unaltered (See Example 8).

Furthermore, the present inventors showed that a water permeable layer being disposed on an external surface of the buffering layer still allows the solid buffer to exert its cellular affects since the water permeable layer allows the redistribution of ions and therefore does not decrease the overall bulk effect of the solid buffer. Thus as illustrated in Example 14, solid buffers may be overlayed with open pore polymers and still exert cytotoxic effects.

Thus, according to one aspect of the present invention there is provided a method of generating a change in a cellular process of a target cell of a multicellular organism, the method comprising contacting the target cell with a solid buffer, so as to alter an intracellular pH value in at least a portion of said cell, thereby generating the change in a cellular process of a target cell of a multicellular organism.

The cells of the present invention may be in any cellular environment e.g. isolated cells, a cell suspension, a cell culture, in a tissue, or in an organism. The cells may be healthy or diseased (e.g. tumor cells) or a combination thereof.

As used herein, the phrase "change in a cellular process" refers to either an up-regulation of down-regulation in a cellular process. Exemplary cellular processes which may be changed according to this aspect of the present invention, include but are not limited to rate of cell death (apoptosis or necrotic cell death), cell differentiation, cell signaling cell growth, cell division, cell differentiation, cell proliferation, tumor growth, tumor vascularization, tumor metastases, tumor metastases migration and/or mobility, cellular mobility, organelle function (including but not limited to, pseudopod formation, flagellar motility, and the like) and molecular transport across various cellular and intracellular membranes and compartments.

According to a particularly preferred embodiment of this aspect of the present invention, the change in a cellular process results in cell killing. Calibrating the solid buffer so that it is able to affect a cytotoxic action is described hereinbelow.

As used herein, the phrase "multicellular organism" refers to any organism containing more than one cell. Exemplary multicellular organisms include eukaryotes (e.g. mammals), and higher plants.

It will be appreciated that the solid buffers of the present invention may also be used to affect cellular processes in prokaryotic cells as well—for example, fungi and gram positive and gram negative bacteria.

The term "Gram-positive bacteria" as used herein refers to bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracis, Bifidobacterium* spp., *Clostridium botulinum, Clostridium perfringens, Clostridium* spp., *Clostridium tetani, Corynebacterium diphtheriae, Corynebacterium jeikeium, Enterococcus faecalis, Enterococcus faecium, Erysipelothrix rhusiopathiae, Eubacterium* spp., *Gardnerella vaginalis, Gemella morbillorum, Leuconostoc* spp., *Mycobacterium abcessus, Mycobacterium avium complex, Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans, Nocardia* spp., *Peptococcus niger, Peptostreptococcus* spp., *Proprionibacterium* spp., *Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae* (group B *streptococcus*), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A *streptococcus*), *Streptococcus salivarius, Streptococcus sanguis*.

The term "Gram-negative bacteria" as used herein refer to bacteria characterized by the presence of a double membrane surrounding each bacterial cell. Representative Gram-negative bacteria include *Acinetobacter calcoaceticus, Actinobacillus actinomycetemcomitans, Aeromonas hydrophila, Alcaligenes xylosoxidans, Bacteroides, Bacteroides fragilis, Bartonella bacilliformis, Bordetella* spp., *Borrelia burgdorferi, Branhamella catarrhalis, Brucella* spp., *Campylobacter* spp., *Chalmydia pneumoniae, Chlamydia psittaci, Chlamydia trachomatis, Chromobacterium violaceum, Citrobacter* spp., *Eikenella corrodens, Enterobacter aerogenes, Escherichia coli, Flavobacterium meningosepticum, Fusobacterium* spp., *Haemophilus influenzae, Haemophilus* spp., *Helicobacter pylori, Klebsiella* spp., *Legionella* spp., *Leptospira* spp., *Moraxella catarrhalis, Morganella morganii, Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Treponema carateum, Treponema pallidum, Treponema pallidum endemicum, Treponema pertenue, Veillonella* spp., *Vibrio cholerae, Vibrio* vulnificus, *Yersinia enterocolitica, Yersinia pestis.*

As used herein, the phrase "solid buffer" refers to any solid material which comprises a buffering capacity. A buffer capacity is defined as the capacity of the buffer to resist changes in its pH when acids or bases are added to the buffer (titration) and is determined by the concentration of $H^+$ ions added per unit volume that may affect a change of 1 pH unit in the buffer system. The buffer capacity of a system is typically derived from the coexistence in the system of dissociated and non dissociated compounds capable of maintaining a constant supply of $H^+$ ions. Accordingly, any acidic or basic substance (i.e. ion exchange material) incorporated in an ion conductive or water/ion permeable matrix may be classified as a solid buffer. The buffer capacity of solid substances is typically derived from the presence of a plurality of functional groups that can release or bind $H^+$ and is determined by the degree of saturation of these substances, namely, the $H^+$ concentration at which all of these functional groups interact.

Exemplary cationic ion exchange materials include, but are not limited to, sulfonic acids and derivatives thereof, sulfonated polystyrene and derivatives thereof, carboxylic acids and derivatives thereof, phosphonic acids and derivatives thereof, phosphinic acids and derivatives thereof, phenols and derivatives thereof, arsenic acids and derivatives thereof, and selenic acids and derivatives thereof.

Exemplary anionic exchange materials include, but are not limited to, compounds comprising quaternary, tertiary, secondary, and primary amines.

Exemplary water permeable matrices include, but are not limited to, open pore polymers, open pore ceramics, and gels.

Exemplary open pore polymers include, but are not limited to, PVOH, cellulose, and polyurethane.

Alternatively, the solid buffer may comprise a matrix which is intrinsically ion conductive. Examples of intrinsically ion conducting solid buffers include, but are not limited to, ionomers and polycationic materials.

Some examples of ionomers that have been commercialized are NAFION™ perfluorinated sulfonic acid membranes and SURLYNT™ thermoplastic resin, both of which are available from available from E. I. du Pont de Nemours & Co., Inc. (Wilmington, Del.).

Typically, the solid buffer is a polymer. It will be appreciated that there is a very wide variety of polymers that may be used as solid buffers according to this aspect of the present invention. Non-limiting examples of such polymers that are useful to the present invention include poly(4-vinyl-N-alkylpyridinium bromide), poly(methacryloyloxydodecyl-pyridinium bromide), poly(vinyl-N-hexylpyridinium), N-alkylated poly(4-vinylpyridine), poly(4-vinyl-N-alkylpyridine), poly(4-vinyl-N-alkylpyridinium bromide), poly(4-vinyl-N-alkylpyridine), poly(N-alkylvinylpyridine), sulfonated polystyrene divinylbenzene (acid form), sulfonated polystyrene, poly(N-alkyl-ethyleneimine), poly(1-chloromethyl-4-vinylbenzene), poly(dimethyloctyl[4-vinylphenyl]methylammonium chloride), poly(di-methyldodecyl[4-vinylphenyl]methylammonium chloride), poly(dimethyltetradecyl[4-vinylphenyl]methylammonium chloride, 50:50 poly(1-chloromethyl)-4-vinylbenzene: poly (dimethyldodecyl[4-vinylphenyl]methylammonium chloride), 50:50 poly(1-chloromethyl)-4-vinylbenzene: poly(dimethyl-octyl[4-vinylphenyl]methylammonium chloride), 50:50 poly (dimethyldodecyl[4-vinylphenyl]methylammonium chloride): poly(dimethyloctyl[4-vinyl-phenyl]methylammonium chloride), poly(tributyl[4-vinylphenyl]methylphosphonium chloride), and poly(trioctyl[4-vinylphenyl]methylphosphonium chloride).

It will be appreciated that the solid buffer of the present invention may also comprise gel matrices such as polyacrylamide and agarose gel matrices which have been suitably prepared with appropriate buffers (e.g. with IMMOBILINE™ acrylamido buffers). Amounts of immobilines pK buffers used that produce gels of a particular pH are set forth in Table 1 of the Example section below. The solid buffers of the present invention may also be ion exchange beads, polymer coated ion exchange beads or ion exchange beads incorporated in an ion permeable matrix.

The term "contacting" as used herein refers to the positioning of the cell with respect to the solid buffer and is confined by the necessity of ions from the solid buffer to be conducted to the cell and vice versa.

A solid buffer is herein disclosed which comprises one or more ion exchange materials. The solid buffer has a volumetric buffering capacity greater than about 20 mM $H^+$/(L.pH unit). When the solid buffer material is in an environment capable of transporting $H^+$ ions, the solid buffer is adapted to cause the death of at least one target cell within or in contact with the environment.

The solid buffer herein disclosed is adapted to cause the death of at least one target cell within or in contact with the environment. The target cell is a bacterial cell, a fungal cell or a yeast cell.

Thus, according to one embodiment of this aspect of the present invention, the cell and the solid buffer are in direct physical contact with one another. For example, the solid buffer may contact the exterior of the cell or adhere to the exterior of the cell. Alternatively, the solid buffer may be internalized by the cell by known processes of internalization of exracellular substances, such as, but not limited to, phagocytosis, endocytosis, receptor mediated endocytosis, clathrin-coated pit or vesicle associated internalization processes, transferrinfection, and the like.

According to another embodiment of this aspect of the present invention, the solid buffer is separated from the cell by a water permeable layer. Such a water permeable layer would allow the flow of ions from the solid buffer to the cell and vice versa and therefore would not impede the buffering capacity of the solid buffer. Exemplary water permeable layers comprise PVOH, ethylcellulose, cellulose acetate, polyacrylamide, any microporous matrix with or without a hydrophilic additive, etc.

An embodiment of the solid buffer herein disclosed is adapted to kill the target cell without inserting any of its structure into the membrane of the target cell.

An embodiment of the solid buffer herein disclosed is characterized by one or more functional groups selected from the group consisting of sulfonic acid, phosphonic acid, quaternary amine, tertiary amine, and derivatives thereof.

An embodiment of the solid buffer herein disclosed is characterized by one or more functional groups selected from the group consisting of carboxylic acid and derivatives thereof, phosphinic acid and derivatives thereof, phenol and derivatives thereof, arsonic acid and derivatives thereof, selenic acid and derivatives thereof, secondary amine and derivatives thereof, and primary amine and derivatives thereof.

An embodiment of the solid buffer herein disclosed comprises sulfonated tetrafluoroethylene copolymer and/or derivatives thereof.

An embodiment of the solid buffer herein disclosed is selected from the group consisting of polyacrylamide-immobilines, agarose-immobilines, poly(diethylaminoethyl acrylate), cationic polyurethane, cationic sub micron silica, and ion exchange beads.

An embodiment of the solid buffer herein disclosed has a volumetric buffering capacity of at least about 50 mM $H^+$/(L.pH unit).

An embodiment of the solid buffer herein disclosed has a volumetric buffering capacity of at least about 100 mM $H^+$/(L.pH unit).

An embodiment of the solid buffer herein disclosed is further characterized by an $H^+$ concentration of greater than about $3.2 \times 10^{-5}$ M or less than about $10^{-8}$ M.

An embodiment of the solid buffer herein disclosed comprises a pH gradient along at least a portion thereof.

An embodiment of the solid buffer herein disclosed comprises the solid buffer with a plurality of regions of differing pH.

An embodiment of the solid buffer herein disclosed comprises ion exchange material is a polymer.

An embodiment of the solid buffer is herein disclosed wherein the ion exchange material comprises cationic silica.

An embodiment of the solid buffer is herein disclosed wherein the solid buffer comprises one or more of an ion exchange bead, a polymer-coated ion exchange bead, and an ion exchange material incorporated in a matrix.

An embodiment of the solid buffer is herein disclosed wherein the solid buffer comprises one or more of a water soluble polymer, a water permeable polymer, an intrinsically ion-conducting polymer, an ion permeable polymer, and a water-permeable ceramic.

An embodiment of the solid buffer is herein disclosed wherein the solid buffer comprises at least a portion of a coating or a component of a medical device, a wound dressing, sutures, cloth, fabric and a wound ointment.

An embodiment of the solid buffer is herein disclosed wherein the solid buffer is in the form of a shaped article, a coating, a spray, a film, a laminate on a film, a film in a laminate, sheets, beads, beads incorporated in fabric, particles, microparticles, microcapsules, microemulsions or nanoparticles.

An embodiment of the solid buffer is herein disclosed wherein the solid buffer is covered by a barrier layer, the barrier layer characterized as being selectively permeable to water.

An embodiment of the solid buffer is herein disclosed wherein the solid buffer is covered by a barrier layer, the barrier layer characterized as being permeable to a preselected target cell but not to preselected non-target cells.

It is a mode of the present invention to provide a composition of matter comprising (a) a solid buffer comprising one or more ion exchange materials, the solid buffer characterized by a volumetric buffering capacity of greater than about 20 mM $H^+$/(L.pH unit); and (b) a selectively permeable barrier layer covering the solid buffer; the composition of matter characterized by being adapted to kill at least one target cell located in an environment capable of transporting $H^+$ ions and in contact with the composition of matter.

It is a mode of the present invention to provide the composition of matter wherein the selectively permeable barrier layer is selectively permeable to water.

It is a mode of the present invention to provide the composition of matter wherein the selectively permeable barrier layer is selectively permeable to a preselected target cell but not to preselected non-target cells.

It is a mode of the present invention to provide the barrier layer comprising at least one form selected from the group consisting of coating, film, and membrane.

It is a mode of the present invention wherein the barrier layer is selected from the group consisting of an open pore polymer, an open pore ceramic and an open pore gel.

It is a mode of the present invention to provide the barrier layer in an open pore polymer selected from the group consisting of one or more of polyvinyl alcohol, cellulose, ethyl cellulose, cellulose acetate, polyacrylamide and polyurethane.

It is a mode of the present invention to provide the composition of matter wherein the target cell is a bacterial cell, a fungal cell or a yeast cell.

It is a mode of the present invention wherein the non-target cells are chosen from the group consisting of (a) mammalian cells, (b) plant cells, and (c) any combination of the above.

It is a mode of the present invention to provide the target cell is a bacterium.

It is a mode of the present invention to provide the solid buffer further characterized by having an $H^+$ concentration of greater than about $3.2 \times 10^{-5}$ M or less than about $10^{-8}$ M.

It is a mode of the present invention wherein the solid buffer has a volumetric buffering capacity of at least about 50 mM $H^+$/(L.pH unit).

It is a mode of the present invention to provide the composition of matter wherein the solid buffer has a volumetric buffering capacity of at least about 100 mM $H^+$/(L.pH unit).

It is a mode of the present invention to provide the composition of matter wherein the solid buffer comprises one or more functional groups selected from the group consisting of sulfonic acid, phosphonic acid, quaternary amine, tertiary amine, and derivatives thereof.

The aforementioned composition of matter is provided wherein the solid buffer comprises one or more functional groups selected from the group consisting of carboxylic acid and derivatives thereof, phosphinic acid and derivatives thereof, phenol and derivatives thereof, arsonic acid and derivatives thereof, selenic acid and derivatives thereof, secondary amine and derivatives thereof, and primary amine and derivatives thereof.

The aforementioned composition of matter is provided wherein the solid buffer comprises at least one substance selected from the group consisting of sulfonated tetrafluoroethylene copolymer and derivatives of sulfonated tetrafluoroethylene.

The aforementioned composition of matter is provided wherein the solid buffer is selected from the group consisting of polyacrylamide-immobilines, agarose-immobilines, poly(diethylaminoethyl acrylate), cationic polyurethane, cationic sub micron silica, and ion exchange beads.

The aforementioned composition of matter is provided wherein the solid buffer is adapted to kill living target cells without inserting any of its structure into an outer cell membrane of the target cell.

The aforementioned composition of matter is provided wherein the barrier layer is adapted to prevent ions larger than H+ and OH− from neutralizing the solid buffer.

The aforementioned composition of matter is provided wherein the wherein the target cell is chosen from the group consisting of bacterial cells, fungal cells, and yeast cells.

The aforementioned composition of matter is provided wherein the target cell is a bacterial cell.

The aforementioned composition of matter is provided wherein the solid buffer kills target cells without inserting any of its structure into the outer membrane of the target cells.

Reference is now made to a method of generating a change in a cellular process of a target eukaryotic cell of a multicellular organism, the method comprising contacting the target cell with a solid buffer so as to alter an intracellular pH value in at least a portion of the target cell, thereby generating the change in a cellular process of a target cell of a multicellular organism.

Reference is now made to a method of generating a change in a cellular process of a target eukaryotic cell, the method comprising contacting the target cell with a solid buffer so as to alter an intracellular pH value in at least a portion of the target cell, thereby generating the change in a cellular process of a target cell.

Reference is now made to the aforemention methods wherein the eukaryotic target cell is a yeast cell.

Reference is now made to the aforementioned methods wherein the contacting is effected in vivo.

Reference is now made to the aforementioned methods wherein the contacting is effected ex vivo.

Reference is now made to the aforementioned methods wherein the contacting is effected in vitro.

Reference is now made to the aforementioned methods wherein generating the change results in death of the target cell.

Reference is now made to the aforementioned methods wherein the solid buffer comprises an anionic ion exchange material incorporated in a water permeable polymer matrix.

Reference is now made to the aforementioned methods wherein the solid buffer comprises a cationic ion exchange material incorporated in a water permeable polymer matrix.

Reference is now made to the aforementioned methods wherein the solid buffer comprises a polymer.

Reference is now made to the aforementioned methods wherein the solid buffer comprises an ionomer.

Reference is now made to the aforementioned methods wherein the solid buffer comprises a sulfonated tetrafluoroethylene copolymer or derivative thereof.

Reference is now made to the aforementioned methods wherein the solid buffer comprises an intrinsically ion conducting matrix.

Reference is now made to the aforementioned methods wherein the solid buffer is attached to an affinity moiety.

Reference is now made to the aforementioned methods wherein the solid buffer is at least partially covered by a selective barrier.

Reference is now made to the aforementioned methods wherein the solid buffer comprises a volumetric buffering capacity greater than about 20 mM H+/ml/pH.

The method of either one of claim 43 or 44, wherein the solid buffer comprises a pH greater than pH 8.

Reference is now made to the aforementioned methods wherein the solid buffer comprises a pH less than pH 4.5.

Reference is now made to the aforementioned methods wherein the solid buffer is attached to at least part of a surface of a support.

Reference is now made to the aforementioned methods wherein the solid buffer comprises a buffering layer and a water permeable layer disposed on an external surface of the buffering layer.

Reference is now made to the aforementioned methods wherein the water permeable layer is an open pore polymer.

Reference is now made to a method of treating a medical condition associated with a pathological cell population, the method comprising administering into a subject in need thereof a therapeutically effective amount of a solid buffer so as to alter at least a portion of an intracellular pH value of the pathological cell population, thereby treating the medical condition associated with the pathological cell population.

Reference is now made to the aforementioned method further comprising the additional step of administering a therapeutically effective amount of the solid buffer to a subject suffering from a medical condition characterized by a pathological cell population, wherein the method provides a treatment for the medical condition.

Reference is now made to the aforementioned method wherein the solid buffer is internalized by the target cell.

Reference is now made to a pharmaceutical composition comprising as active ingredient a solid buffer and a pharmaceutically acceptable carrier or diluent.

Reference is now made to the pharmaceutical composition wherein the solid buffer is formulated in particles.

Reference is now made to an article of manufacture comprising (i) a support; and (ii) a solid buffer layer being attached to at least part of a surface of the support, the solid buffer comprises a buffering layer and an ion permeable layer being disposed on an external surface of the buffering layer.

Reference is now made to an article of manufacture comprising (i) a support; and (ii) a solid buffer layer being attached to at least part of a surface of the support, the solid buffer being anionic.

As mentioned hereinabove, the solid buffers of the present invention may be formulated for generating a change in a particular cellular process. Typically, three properties of the solid buffer may be manipulated so as to allow the solid buffer to affect a cellular process –pH, buffer capacity, and ion conductivity.

The following is an example of how a solid buffer may be selected in order to affect (e.g. increase) the process of cell death:

1. The pH of the solid buffer should be out of range of the viability of the cell. The range is specific for each type of cell and bacterium. Typically, a pH of less than 4 or greater than 8 of the solid buffer will affect the pH stability of the cell.

It will be appreciated that the solid buffer may be formulated so that it comprises a pH gradient. The gradient may be useful in providing a gradual change in the biological effect of the solid buffer on the cells. For example, using such gradients on solid buffers may result in part of the solid buffer having cytostatic effects on cells while other regions of the solid buffer having cytotoxic effects.

It will be appreciated by those skilled in the art that variations in the form, strength, position and overall pattern of such gradients may be effected by suitably controlling ion exchange materials incorporated in the matrix of the solid buffer, all of which are contemplated to be included within the scope of the present invention. Gradiented buffers may be synthesized using Immobiline™ as described in the Examples section hereinbelow.

Furthermore, it will be appreciated that the solid buffer of the present invention may also comprise a combination of cationic ion exchange materials and anionic ion exchange materials arranged in a pattern suitable for effective killing.

Thus the solid buffer may for example comprise a mixture of anionic and cationic beads. The beads may be of the same size or different size depending on the positioning of the target cells.

2. Since the generally accepted values for buffer capacity of the cytosol and most other cellular components is between 20-100 mM $H^+$/liter.pH, therefore to cause titration of the cytosol, the buffer capacity of the solid buffer material should be higher than this value. A typical buffering capacity of the solid buffer that may be used to kill most cell types is about 100 mM $H^+$/liter.pH or higher.

3. A change in the ion conductivity (proton conductivity) of a solid buffer will affect the speed with which the solid buffer is able to kill a cell. Typically, the ion mobility in a water permeable solid buffer will be determined by the diffusional movement of protons in water and will be of the order of about $10^{-8}$ $m^2$/sec for the diffusion constant, this corresponding to a drift velocity of 0.1 mm/sec. Such solid buffers will induce cell death in a cell in contact in a matter of seconds.

Thus, an exemplary method for killing a cell is by contacting the cell with a solid buffer comprising a buffer capacity of about 50 mM $H^+$/liter.pH and a pH capable of titrating the cell, thereby inducing cell death, the pH being generally greater than pH 8, or less than pH 4.5.

Methods of measuring pH and determining buffering capacity are well known in the art.

It will be appreciated the plasma buffering capacity of cells and pH is cell-type specific and therefore manipulation of these parameters may allow targeting to a particular cell type. For example, it is generally accepted that tumor cells are more alkaline than normal cells and thus in order to exert an optimal cytotoxic activity in tumor cells, the solid buffer may have less (or no) effect on other cell types. In addition, each cell type has a particular membrane permeability and therefore may inherently be more (or less) susceptible to the solid buffers of the present invention.

As a further example, it is known that the buffer capacity of bacteria is higher than in mammalian cells but the vulnerability of bacteria to titration by buffers is higher since the mass of the buffering medium in bacteria is about three orders of magnitude smaller than in mammalian cells. This makes possible to use low buffer capacity solid buffers to kill bacteria without killing mammalian cells One method of altering the pH and buffering capacity of solid buffers is by changing the concentration of an ion exchange material in a water soluble (ion permeable) matrix. Alternatively, the concentration of the ion exchange material may remain constant and the ion exchange material may be altered. An optimal solid buffer may be selected for killing a cell of interest by testing a plurality of solid buffers comprising differing pHs and buffering capacities on a mixture of cells including the cell of interest. The cell of interest may then be analyzed to determine the optimal solid buffer. Methods of analyzing the cell of interest may include microscopy, immunohistochemistry or other biological assaying techniques known in the art.

Since the present invention contemplates using solid buffers to treat medical conditions (e.g. one associated with a pathological cell population), the solid buffer is typically administered to the body, either in vivo or ex vivo, and it is therefore particularly important that the solid buffers are able to selectively target specific cell types.

Thus, according to an embodiment of this aspect of the present invention, the solid buffer may be attached to an affinity moiety, such as an antibody, a receptor ligand or a carbohydrate. Examples of antibodies which may be used according to this aspect of the present invention include but are not limited to tumor antibodies, anti CD20 antibodies and anti-IL 2R alpha antibodies. Exemplary receptors include, but are not limited to folate receptors and EGF receptors. An exemplary carbohydrate which may be used according to this aspect of the present invention is lectin.

The affinity moiety may be covalently or non-covalently linked to or adsorbed onto to the solid buffer using any linking or binding method and/or any suitable chemical linker known in the art. The exact type and chemical nature of such cross-linkers and cross linking methods is preferably adapted to the type of affinity group used and the nature of the solid buffer. Methods for binding or adsorbing or linking such affinity labels and groups are also well known in the art.

In accordance with one preferred embodiment of the present invention, the target cells may be metastasized cancer cells expressing identifiable surface markers. If the pH and buffer capacity of the solid buffer are selected to kill such cells upon contact, the affinity moieties may be one or more antibodies directed against specific markers expressed by such malignant cells.

Another method of targeting specific cell types (e.g. targeting prokaryotic cells and not eukaryotic cells) contemplated by the present inventors is based on selectively preventing the physical contact between the solid buffer and particular cell types. Thus, according to another embodiment of this aspect of the present invention, the solid buffer is at least partially covered by a selective barrier. For example, if the surface of the solid buffer is covered or protected with a mechanical barrier having a controlled pore size (such as but not limited to a filter e.g. nylon filter, having a selected pore size, or a mesh with a selected opening size, or the like), it is possible to exclude cells above a certain size from attaching to or forming contact with the solid buffer, while still allowing cells having a smaller size to enter the pores or to pass the mechanical barrier and to make contact with the solid buffer.

Targeting the solid buffers of the present invention can also be achieved by using "passive" targeting. This exploits the enhanced permeability of and retention of particles in tumor tissue due to leaky vasculature and lack of lymphatic drainage. It is known in the art that the selectivity for tumor for particles of size 200-600 nanometer is between 10 to 100 fold relative to healthy tissue. This particular type of passive targeting may make use of particles which are not functionalized by recognition groups or moieties.

The solid buffer of the present invention can be administered to an organism per se, or in a pharmaceutical composition where it is mixed with suitable carriers or excipients.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

As used herein, the term "active ingredient" refers to the solid buffer accountable for the intended biological effect.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

The solid buffer of the present invention may be formulated as particles or beads and may be manufactured in mean sizes within the range of several nanometers to few millimeters and larger.

The solid buffer may be attached on the particle surface or encapsulated within the particles. It will be appreciated that if the solid buffer is held within the particle, the encapsulating particle must be made of an ion conducting material to allow the flow of ions between the solid buffer and the cell. Exemplary particles include, but are not limited to polymeric particles, microcapsules liposomes, microspheres, microemulsions, nanoparticles, nanocapsules and nanospheres.

The solid buffers of the present invention may also be coated by biodegradable coatings in order to improve selectivity and prevent activity while in circulation. Exemplary biodegradable coatings include Polyethylenimine (PEI) coatings, polyethylene glycol (PEG) coatings modified gelatin coating or any other suitable coating material.

Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For topical administration, the solid buffer of the present invention may be formulated as a gel, a cream, a wash, a rinse or a spray. This may be applied when the solid buffer is administered topically to a subject or onto any solid surface.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., a nucleic acid construct) effective to prevent, alleviate, or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

It will be appreciated that the present invention also contemplates coating a solid surface or material with the solid buffer of the present invention. The term "surface" as used herein refers to any surface of any material, including glass, plastics, metals, polymers, and like. It can include surfaces constructed out of more than one material, including coated surfaces.

The solid buffer may be attached to a surface using any method known in the art including spraying, wetting, immersing, dipping, painting, ultrasonic welding, welding, bonding or adhering or otherwise providing a surface with the solid buffer of the present invention. The solid buffers of the present invention may be attached as monolayers or multiple layers.

An exemplary solid surface that may be coated with the solid buffers of the present invention is an intracorporial or extra-corporial medical device or implant.

An "implant" as used herein refers to any object intended for placement in a human body that is not a living tissue. The implant may be temporary or permanent. Implants include naturally derived objects that have been processed so that their living tissues have been devitalized. As an example, bone grafts can be processed so that their living cells are removed (acellularized), but so that their shape is retained to serve as a template for ingrowth of bone from a host. As another example, naturally occurring coral can be processed to yield hydroxyapatite preparations that can be applied to the body for certain orthopedic and dental therapies. An implant can also be an article comprising artificial components.

Thus, for example, the present invention therefore envisions coating vascular stents with the solid buffers of the present invention. The solid buffers may repel or attract specific type of proteins in cells which may affect the cell cycle of endothelial cells in contact with the surface to reduce or prevent restenosis, or general type of implants coated by the method of the present invention to achieve beneficial effect in the integration of the implant with tissue.

Another possible application of the solid buffers of the present invention is the coating of surfaces found in the medical and dental environment.

Surfaces found in medical environments include the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; blood filters, implantable medical devices, including artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherably insertable central venous catheters, dialysis catheters, long term tunneled central venous catheters peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, aneurysm repair devices, heart valves, artificial joints, artificial larynxes, otological implants), anastomotic devices, vascular catheter ports, clamps, embolic devices, wound drain tubes, hydrocephalus shunts, pacemakers and implantable defibrillators, and the like. Other examples will be readily apparent to practitioners in these arts.

Surfaces found in the medical environment include also the inner and outer aspects of pieces of medical equipment, medical gear worn or carried by personnel in the health care setting. Such surfaces can include counter tops and fixtures in areas used for medical procedures or for preparing medical apparatus, tubes and canisters used in respiratory treatments, including the administration of oxygen, of solubilized drugs in nebulizers and of anesthetic agents. Also included are those surfaces intended as biological barriers to infectious organisms in medical settings, such as gloves, aprons and faceshields. Commonly used materials for biological barriers may be latex-based or non-latex based. Vinyl is commonly used as a material for non-latex surgical gloves. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered.

Other surfaces related to health include the inner and outer aspects of those articles involved in water purification, water storage and water delivery, and those articles involved in food processing. Thus the present invention envisions coating a solid surface of a food or beverage container to extend the shelf life of its contents.

Surfaces related to health can also include the inner and outer aspects of those household articles involved in providing for nutrition, sanitation or disease prevention. Examples can include food processing equipment for home use, materials for infant care, tampons and toilet bowls.

As illustrated in Example 15, the solid buffers of the present invention may be used to enhance the antibacterial activity of a wound dressing. Similarly, the solid buffers of the present invention may be used to enhance the antibacterial activity in sutures, cloth, fabrics and wound ointments.

In accordance with another embodiment of the present invention, the solid surface may be a microscopic slide, a culturing hood, a Petri dish or any other suitable type of tissue culture vessel or container known in the art.

As used herein, the term "about" refers to plus or minus 10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Distribution of Proteins in a pH Gradient

The following experiment was carried out in order to ascertain whether proteins comprise specific pH characteristics.

Materials and Methods

Gel preparation: Four immobiline gel strips measuring approximately seven centimeters were used. Each strip was cut from an ampholine containing polyacrylamide based gel having a pH gradient from 4-9 prepared as is known in the art (the gel contained 4% polycacrylamide and 5% bisacrylamide cross linker).

Protein solution preparation: Four different protein solutions were prepared. The first solution contained 1.0 mg/ml myoglobin (commercially available from Sigma, USA—catalogue number M-0630) in DDW. The second solution contained 1.0 mg/ml myoglobin in DDW including a final concentration of 8M Urea for protein denaturation. The third solution contained 1.0 mg/ml phycocyanin (commercially available from Sigma, USA as Catalogue Number P-2172) in DDW. The fourth solution contained 1.0 mg/ml phycocyanin in DDW including a final concentration of 8M Urea for protein denaturation. All protein solutions had a pH of about 7.0.

Experimental Procedure: Ten ml of each of the above described protein solutions were placed in a Petri dish and a strip of gel was immersed into each one. The Petri dishes were covered and the gels were incubated for 3-5 days at room temperature. At the end of the incubation period, the gel strips were removed from the Petri dishes, carefully blotted from excess liquid and scanned in an Epson flatbed office scanner.

Results

As illustrated in FIGS. 1A-B and 2A-B, the proteins were adsorbed differently into different regions of the gel strips according to the pH at the different regions of the strip.

Figure 1B:
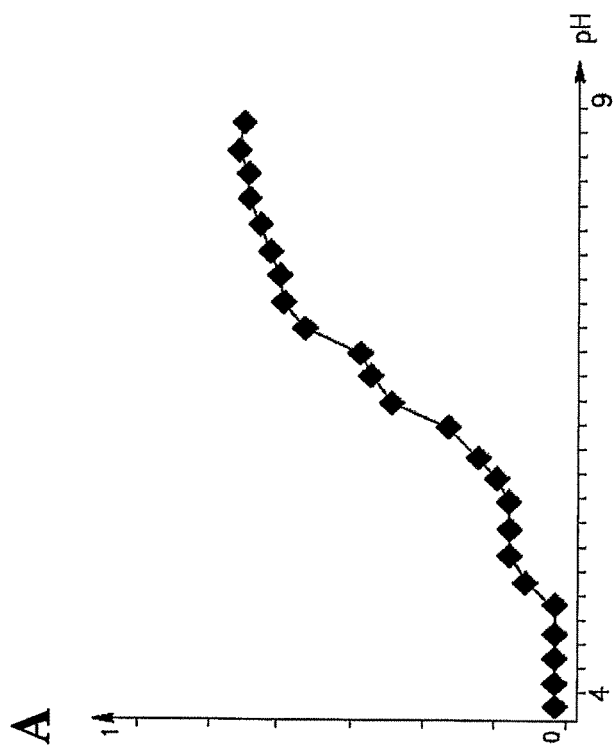
Figure 2A:
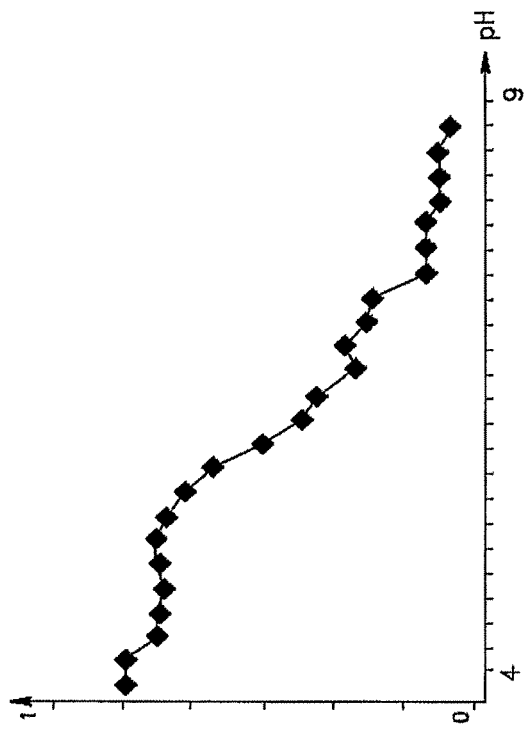
FIGS. 2A-B are graphs illustrating the spatial distribution of the native and urea denatured forms of the protein myoglobin in strips containing polyacrylamide based gels having a pH gradient. The graph of FIG. 2A represents the results of the scan for native (non-denatured) myoglobin. The graph of FIG. 2B represents the results of the scan for 8M Urea denatured myoglobin. The vertical axes represent the Absorbance in O.D. units and the horizontal axes represent the position on the scanned gel strip expressed in pH units.
Figure 2B:
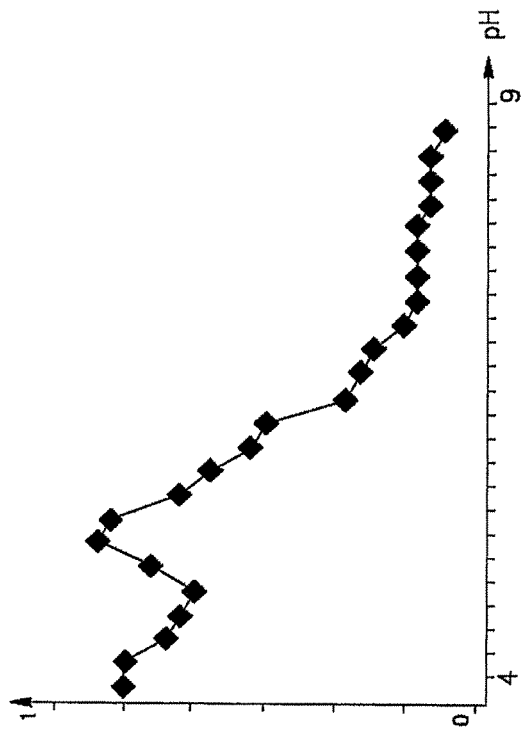

Myoglobin has a pI≈6 and Phycocyanin has a pI≈4.2. While the shift of the spatial (and pH dependent) distribution curve for myoglobin between native and denatured protein is rather small (FIGS. 2A-2B), a very strong shift (difference in spatial distribution of absorbance as a function of pH along the gel strip) is observed for the much larger protein Phycocyanin (FIGS. 1A-1B).

Conclusion

The distribution of a protein in a pH gradient presents a property which is specific for each tested protein and may be presented as a pH characteristic of the protein.

Example 2

Figure 3A:
FIGS. 3A-B are photographs representing two different stages of the results of an experiment demonstrating pH dependent separation and redistribution of the two different proteins myoglobin and phycocyanin.
Figure 3B:
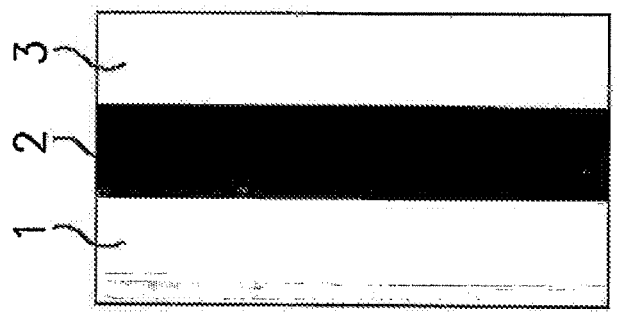

Redistribution of Proteins Across a Gel Membrane According to their pH Characteristics Materials and Methods Gel preparation: A rectangular chamber was divided into three compartments by placing two gel membranes, formed as 2 mm thick polyacrylamide-based gel slabs, as illustrated in FIGS. 3A-B. The gels were prepared by addition of 10 μl of Imobiline™ (Amersham), 0.5 μl ammonium persulfate (APS), 0.25 μl TEMED (1:10), 10% polycarylamide and 5% bisacrylamide. One gel membrane was prepared for pH 4 (acidic, Polyacrylamide with Immobilines) and the other gel membrane was prepared for pH 6 (basic, Polyacrylamide with Immobilines).

Protein solution preparation: Myoglobin and Phycocyanin were dissolved in doubly deionized water (DDW) each at a concentration of 0.1 gram/Liter (g/L).

Experimental Procedure: 300 μl of each protein solution was placed into the central chamber bordered by the two membranes. The chamber on the acidic side was filled by a buffer solution of 1 mM of glutamic acid (pH=3.8) and the chamber at the basic side was filled with 1 mM solution of TRIS (pH=8.3). The chamber was left undisturbed at room temperature. After several days, the chamber was visually observed and also photographed (top view) using a digital camera.

Results

At the beginning of the experiment the solution in the middle compartment 2 of the multi compartment chamber described above has a dark color resulting from the combined absorbance of the myoglobin and phycocyanin present in the middle compartment 2, while there was hardly any color observed in the compartments labeled 1 and 3 which contained the acidic (1 mM of glutamic acid; pH=3.8) buffer and the basic buffer (1 mM solution of TRIS; pH=8.3), respectively, as illustrated in FIG. 3A.

As illustrated in FIG. 3B, by the end of the experiment, the solution in the middle compartment 2 of the multi compartment chamber described above had a much fainter magenta-like color resulting from the combined absorbance of a much lower concentration of myoglobin and phycocyanin left therein. A strong reddish color was observed in the compartment labeled 1 which contained the acidic (1 mM of glutamic acid; pH=3.8) buffer into which a large portion of the myoglobin migrated. A strong bluish color was observed in the compartment labeled 3 which contained the basic buffer (1 mM solution of TRIS; pH=8.3), into which a large portion of the phycocyanin migrated.

Conclusion

An almost complete redistribution and separation of the two colored proteins occurred governed by the different pH values in the compartments separated by the Imobiline™ membranes.

Example 3

The following experiment was carried out to demonstrate the feasibility of affecting intracellular distribution of a cytoplasmic protein within a living functioning cell.

Materials and Methods

HeLa cells were transfected to express GFP in their cytosol. Following lysis, the extracted proteins were tested to determine the pH region of maximum accumulation of the GFP protein as described in Example 1 above. The region of maximum accumulation of the GFP protein (as determined by locating the peak fluorescence on the scanned gel strip) was found to be at about pH=9.

Commercial polyacrylamide beads having a mean diameter of approximately 50 microns (Biogel P10, Cat. No. 1504140, Biorad, USA) were soaked in a solution of a copolymer of polyacrylamide and immobilines at pH=9 (prepared as detailed in Example 2 hereinabove). The Imobiline™ polyacrylamide solution was allowed to chemically polymerize following which an aqueous suspension of the resulting beads was added to a cell culture of the HeLa cells expressing GFP. Some of the cells attached themselves to the beads. The mixture of cells and beads was then immobilized by casting an agarose solution (Low melt agarose, catalogue Number 1620019 Biorad, USA and having a melting point of about 36° C.) on the cells and the beads, and allowing the agarose to cool to about 25° C. A cell in contact with a bead was observed under a fluorescence microscope (Axioscope 2 Fluorescence Microscope, Zeiss, Germany) and the change of distribution of the GFP was visually and photographically monitored over a period of 30 minutes.

Results

As may be seen in FIGS. 4A-C, the fluorescence intensity at the point of attachment of the cell to the bead was about fifty times higher 30 minutes following initial attachment than the initial intensity in the cell as measured at time zero. This measured intensity accounts for a major fraction of the GFP in the cell. A similar phenomenon was observed in several cells which were attached to the beads.

Control experiments with similar beads having coating with pH=7 (not shown) did not show any change in the distribution pattern of GFP in cells attached to the beads and similarly observed.

Conclusion

The above experimental observations clearly demonstrate that a localized protein (GFP) accumulation or redistribution mechanism based on pH partitioning may be induced in a living cell and that it is possible to generate a concentration gradient or a localized concentration of an intracellular protein using contact with a material or object which has a controlled pH at it's surface. The experiment also demonstrates that this property can be utilized to cause redistribution of one or more proteins in a living cell.

Example 4

Effect of pH on Cytotoxicity of Yeast Cells

This experiment was performed to test the cytotoxicity of pH modified surfaces on yeast cells.

Materials and Methods

The bottom of nine plastic Petri dishes were coated with a 0.5 mm thick polyacrylamide gel with immobilines (acrylamido buffers), each gel having a different pH from the preceding gel by about 1 pH unit. The coating of the first dish was a pH 3 acrylamido Imobiline™ buffer gel, the coating of the second dish was a pH 4 acrylamido Imobiline™ buffer gel, the coating of the third dish was a pH 5 acrylamido Imobiline™ buffer gel etc., . . . , and the coating of the ninth dish was a pH 11 acrylamido Imobiline™ buffer gel.

The coating was prepared by standard polymerization methods as is known in art. The composition of imobilines is set forth in Table 1 hereinbelow:

TABLE 1

| | IMMOBILINE pK BUFFERS USED (µl) | | | | | |
|---|---|---|---|---|---|---|
| pH | 3.6 | 4.6 | 6.2 | 7.0 | 8.5 | 9.3 |
| 3.00 | 256 | 0 | 4 | 0 | 0 | 0 |
| 4.00 | 276 | 103 | 59 | 0 | 0 | 170 |
| 5.00 | 295 | 200 | 111 | 0 | 0 | 331 |
| 6.00 | 295 | 200 | 111 | 0 | 0 | 331 |
| 7.00 | 130 | 532 | 90 | 188 | 0 | 551 |
| 8.00 | 0 | 605 | 0 | 273 | 147 | 476 |
| 9.00 | 219 | 0 | 212 | 231 | 72 | 284 |
| 10.0 | 0 | 40 | 0 | 1138 | 85 | 237 |
| 11.0 | 0 | 1 | 0 | 1345 | 99 | 335 |

The numbers in table 1 are given as µl of starting material (having a concentration of 100 mM) used to prepare 10 ml of pH solution by addition of DDW.

1-2 Million yeast cells Sacharomices (commercially available baker's yeast), suspended in tissue culture medium (Roswell Park Memorial Tissue Culture Media, RPMI-1640 Dutch Mod. 01-1-7-1) were placed in each of the Petri dishes. The cells sedimented to the bottom of the dish and came in contact with the polyacrylamide surface and were left in the dish for a preset time as indicated Table 2 hereinbelow. Following the indicated contact time, the cells were stained using Trypan Blue and the number of dead cells was estimated for each dish.

Results

Table 2 below lists the cell mortality data (as % of total cells) at the indicated pH and exposure time.

TABLE 2

| | Time (hours) | | | | | | |
|---|---|---|---|---|---|---|---|
| pH | 0.25 | 0.5 | 1 | 2 | 4 | 6 | 12 |
| 3 | 50 | 100 | 100 | 100 | 100 | 100 | 100 |
| 4 | 25 | 25 | 50 | 55 | 80 | 100 | 100 |
| 5 | 2.5 | 15 | 25 | 45 | 65 | 95 | 97.5 |
| 6 | 1.5 | 15 | 25 | 35 | 50 | 55 | 60 |
| 7 | 1.5 | 2.5 | 5 | 3 | 1.5 | 5 | 1 |
| 8 | 2.5 | 2.5 | 5 | 3.5 | 1.5 | 4 | 2.5 |
| 9 | 5 | 55 | 45 | 55 | 70 | 80 | 85 |
| 10 | 25 | 50 | 50 | 60 | 85 | 95 | 99 |
| 11 | 50 | 100 | 100 | 100 | 100 | 100 | 100 |
| Control (Pure PA) | 1.5 | 2.5 | 3.5 | 2.5 | 1.5 | 4 | 3.5 |

As may be seen from Table 2, at extreme pH values (pH 3, pH 4, pH10, and pH 11) the cells die within a relatively short time of contact with the pH controlling substrate. At pH 7 and pH 8, no significant cell toxicity is observed even after a prolonged time. At intermediate pH values (in the range of pH 5-9), a time dependent toxicity is observed.

Conclusion

The only parameter that was changed in the gels was the composition of the acrylamido buffers. Since the gel is very stable under aqueous soaking, no release of any kind of toxic agent into the cell culture media can be envisioned. Therefore, the cell toxicity as observed is most probably due to the redistribution of ions (charged proteins, hydrogen ions, potassium ions, and other intracellular ions) in the cell on contact with the surface of the pH controlling acrylamide gels used in the experiment. This assumption is further supported by the fact that if one compares the compositions and toxicity as observed at pH 3, 4, 5 and 6 the concentration of the highly acidic component is almost constant while the toxicity changes are very significant. The same can be observed on the basic side where the concentration of the most basic component changes only slightly for pH 11, 10, 9 and 8 whereas the toxicity changes significantly.

This observation proves that the toxicity is not the result of incorporation of the highly anionic or cationic species as claimed in prior art but the result of the bulk pH property.

The results of this experiment further demonstrate that the rate of cell mortality (delayed cytotoxicity effect) can be controlled by the choice of the pH value in the pH controlling substance or substrate in contact with the cells, and that such effects (the rate of cell death) can be fine tuned by suitably modifying the pH values of the surface or substrate contacting the cells.

Example 5

Effect of pH Induced Cytotoxicity in Jurkat Cells

Materials and Methods

Jurkat cells, Clone E6-1 were grown in RPMI 1640 supplemented with 2 mM L-glutamine, 10 mM HEPES, 10 mM sodium pyruvate and 10% PBS. The cells were exposed to varying pH surfaces as described for yeast cells hereinabove (Example 4).

Results

Table 3 below lists the cell mortality data (as % of total cells) at the indicated pH and exposure time. The results demonstrate high cell toxicity of the surfaces having low and high pH.

TABLE 3

| | TIME (hours) | | |
|---|---|---|---|
| pH | 1 hour | 2 hours | 3 hours |
| 3 | 15 | 90 | 90 |
| 4 | 8 | 20 | 80 |
| 5 | 11 | 5 | 3 |
| 6 | 0 | 0 | 0 |
| 7 | 0 | 3 | 3 |
| 8 | 5 | 10 | 7 |
| 9 | 9 | 9 | 6 |
| 10 | — | — | — |
| 11 | 3 | 12 | 80 |
| Control, Pure PA | 0 | 0 | 0 |

Example 6

Absorption Characteristics of Yellow Fluorescent Protein (YFP)

Materials and Methods

1 µg of H1299 lung cancer cells expressing a yellow fluorescent protein (Source—*Phialadium* sp. SL-2003) were lysed. The extracted proteins were tested to determine the pH region of maximum accumulation of the YFP on an IPG strip (Amersham Biosciences, Immobiline™ Dry Strip pH 3-10). The strip was immersed in the solution for 22 hours, following which it was scanned with a UV scanner of a Zeiss Axiscope 2 Plus, UV microscope.

Results

Figure 5:
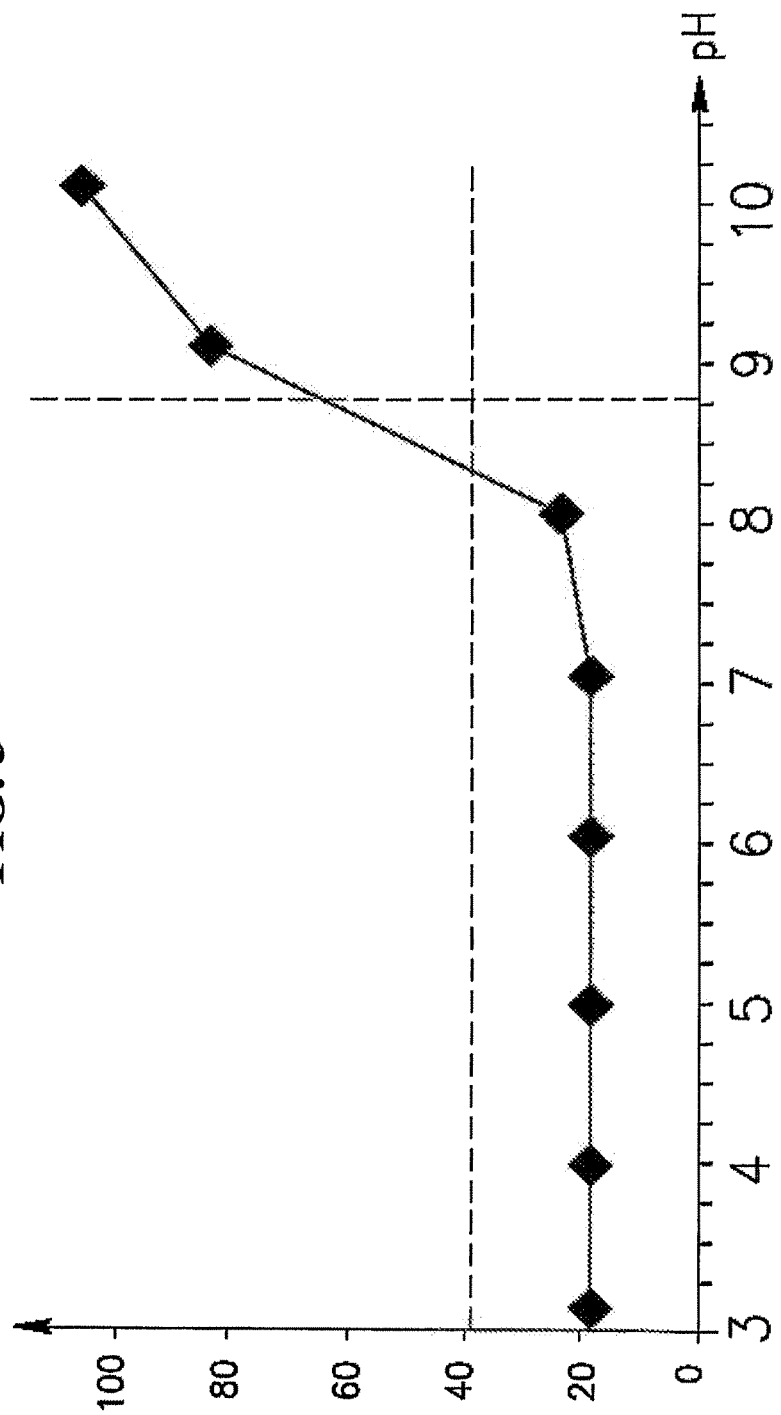
FIG. 5 is a graph illustrating the spatial distribution of Yellow fluorescent protein (YFP) on strips of immobiline containing polyacrylamide based gels having a pH gradient. The vertical axis represents optical density, and the horizontal axis represents the position along the IPG strip expressed in pH units.

As can be seen in FIG. 5, a pH range of 9.5-10 showed the strongest accumulation of the YFP.

Example 7

Physical or Mechanical Barriers Prevent pH Induced Cytotoxicity

The following experiment was designed in order to ascertain whether pH-induced cytotoxicity requires direct contact of the cell with the surface of the pH controlling substrate.

Materials and Methods

A 0.5 mm thick layer of pH 3 immobiline Polyacrylamide gel (IPG) was cast on the bottom of a Petri dish. A 10 µM thick nylon filter with a 2 µM mean pore size (commercially available from Nalgene, USA) was placed in close contact with the surface of the IPG layer.

A suspension of 0.2 million yeast cells in tissue culture medium (Roswell Park Memorial Tissue Culture Media, RPMI-1640 Dutch Mod. 01-1-7-1), was placed in the Petri dish and the cells were left to sediment for six hours. At the end of the six hour sedimentation period, the cells were stained with Tryptan Blue.

Results

The number of dead cells counted was approximately 5% of the total number of cells counted.

Conclusion

The nylon filter interposed between the cells and the surface of the pH controlling substrate, prevented the pH-induced cytotoxicity.

Example 8

Differential Cell Toxicity Device

In order to further establish that direct contact between a cell and the pH controlling substrate is required for pH-induced cytotoxicity, a filter allowing bacteria cells to be in contact with the substrate, while not allowing yeast cells to be in contact with the substrate was used as follows:

Materials and Methods

A 0.5 mm thick layer of pH 3 immobiline Polyacrylamide gel (IPG) was cast on the bottom of a Petri dish. A 10 µm thick nylon filter with a 2 µm mean pore size, as described in Example 6 above, was placed in close contact with the surface of the IPG layer. A mixture of *E. Coli* (100 units/microliter) and Yeast cells (1 million/ml) suspended in 0.5 mls of cell culture medium was placed in the Petri dish on top of the nylon filter and the dish was incubated for a period of 12 hours at 37° C. Following the incubation period, the culture medium was sampled for bacterial colonies on McConkey Agar. The yeast cells were then stained with Tryptan Blue for performing dead cell count.

Results

No bacterial colonies were detected and no significant yeast cell mortality was observed.

Conclusion

The results of this experiment demonstrate that bacterial cells which were in contact with the cytotoxic agent were killed, whereas the yeast cells which were not in contact with the cytotoxic agent remained alive. The results of this experiment further demonstrate the bacterio-toxic property of the pH controlling substrate.

Example 9 pH Induced Cytotoxicity in Jurkat Cells

In order to establish whether pH-induced cytotoxicity occurs in Jurkat cells, the following experiment was performed.

Materials and Methods

A suspension of Polyacrylamide based beads having an approximate mean bead size of about one micron was prepared from a polyacrylamide+Immobiline™ mixture having a pH of 9.0. The beads were added to one million Jurkat cells suspended in 1 ml of tissue culture medium such that the ratio of beads to cells was approximately 20 beads per Jurkat cell. Aliquots were drawn out at 0.5, 1.0 and 2.0 hours following addition of the beads to the cell suspension. The cells were stained with Tryptan Blue dye and the number of dead cells and total cells was counted.

Results

At 0.5 hours following bead addition, the fraction of dead cells in the sample was 5%. At 1.0 hour following addition of the beads to the cells, the fraction of dead cells in the sample was 10%. At 2.0 hours following addition of the beads to the cells, the fraction of dead cells in the sample was 27%.

Example 10

Cytotoxic Effect of Nafion

Sulfonated tetrafluorethylene copolymers (e.g. Nafion) are acidic (anionic charged) bioactive polymers with strong buffering properties and high buffering capacities. These types of films consist of a substrate (e.g. polymethylacrylate, nylon or polyester) and a sulfonated polymer as an active layer. Nafion is not recognized as cytotoxic or bactericidal and is generally used as an ion conductive electrode in fuel cell applications. The following toxicity tests were performed to ascertain whether Nafion is toxic to cells.

Materials and Methods 1 million Jurkat cells in PBS buffer were deposited on a 1 cm square of a nafion commercial membrane (NAFION 117, Perfluorinated membrane, Sigma, 274674-1EA). In order to differentiate between live and dead cells, the membrane was stained with 1 µl of 1 µg/µl of Propidium iodide or trypan Blue.

Results

Figure 6A:
FIGS. 6A-B are photomicrographs illustrating the cytotoxic effect of Nafion film on Jurkat cells.
Figure 6B:

Following a 10 minute exposure to the nafion, more than 95% of cells were dead as seen in FIGS. 6A-B.

Example 11

Bacteriotoxicity and Cytotoxicity of Laminates

Materials and Methods

Laminate samples: laminate samples consisted of films coated on a 110 µm polyester base.

Series BIOACT 13, 15 and 16:

BIOACT 16: 110 µm polyester base+a primer layer of acrylic modified polyurethane.

BIOACT 13: 110 µm polyester base+a primer layer of acrylic modified polyurethane+"active" cationic submicron silica in PVOH binder (w/w ratio 4:1); total coating weight of 0.97 g/m², coating pH 4.06.

BIOACT 15: 110 μm polyester base+a primer layer of acrylic modified polyurethane+"active" cationic polyurethane polymer in PVOH binder (w/w ratio 4:1); total coating weight of 0.76 g/m², coating pH 4.

Uncoated sample was provided as control.

Series MVC/HT/56 A, B and C: This set of laminates was based on the incorporation of p-Toluenesulphonic acid salt (pH 3) of poly(diethylaminoethylmethacrylate) as the active component of the coatings.

MVC/HT/56 A: 110 μm polyester base+PVOH+p-Toluenesulphonic acid salt. The total dry coating weight 0.9 gsm (~0.9 microns) of which the dry coat weight of the active component is 0.6 gsm.

MVC/HT/56 B: Identical to MVC/HT/56 A, but a different batch.

MVC/HT/56 C: 110 μm polyester base+PVOH+p-Toluenesulphonic acid salt. The total dry coating weight 0.58 gsm (~0.5 microns) of which the dry coat weight of the active component is 0.24 gsm.

MVC/HT/56 D Identical to MVC/HT/56 A, but a different batch.

Preparation of live and dead Bacterial Suspensions: 10 ml of *E. coli* DH5 were grown to late log phase in LB broth. 1 ml of the culture was concentrated by centrifugation at 5000 rpm for 5 minutes. The pellet was resuspended in 100 μl of 0.85% NaCl. 50 μl of this suspension was added to 950 μl of 0.85% NaCl (for live bacteria) or 850 μl of 70% 2-propanol (for dead bacteria). Both samples were incubated at RT for 1 hour, following which they were pelleted by centrifugation at 5000 rpm for 5 minutes. The obtained pellets were resuspended in 500 μl of 0.85% NaCl and re-centrifuged. Finally, both pellets were resuspended in 50 μl 0.85% NaCl.

Staining of Live and Dead bacterial suspensions: Staining was performed with LIVE/DEAD® BacLight™ Bacterial Viability Kit (Molecular probes). With a mixture of SYTO9 and propidium iodide stains, bacteria with intact cell membranes stain fluorescent green, whereas bacteria with damaged membranes stain fluorescent red. Essentially, 2 μl of SYTO 9 dye, 1.67 mM/Propidium iodide and 1.67 mM Component A was mixed with 2 μl of 1.67 mM/Propidium iodide, 18.3 mM Component B. 0.15 μl of the dye mixture was added to 50 p. 1 of the bacterial suspensions. 2.5 p. 1 of the stained bacteria was trapped between a slide and coverslip. Live and killed cells were observed under a fluorescence microscope.

Antibacterial activity testing of films: Two series of tests were performed using non activated (from the shelf) films and films treated for 20 minutes in a 1M NaCl solution. In both of them the antibacterial activity was estimated by counting under a fluorescent microscope the numbers of dead and live stained bacteria in the sample deposited on the bioactive film.

Cytotoxic activity testing of films: Live and dead Jurkat cells were counted following exposure to the bioactive films by the following procedure: 0.15 μl of the dye mixture was added to 1 million Jurkat cells in 50 μl PBS. 2.5 μl of the stained cells were trapped between an activated film and coverslip. Live and dead cells were observed under a fluorescence microscope.

Results

Antibacterial activity testing of MVC HT 56A, B, C and D: Following a 30 minute incubation of Jurkat cells with the laminates described hereinabove, live (moving) cells were observed in control, MVC/HT/56/B film and MVC/HT/56/D film, which under a green filter (5-2) were green or reddish. In comparison, after 1 minute of incubation on MVC/HT/56/A and /56C laminates all cells were attached and under a green filter were observed as red.

Figure 7:
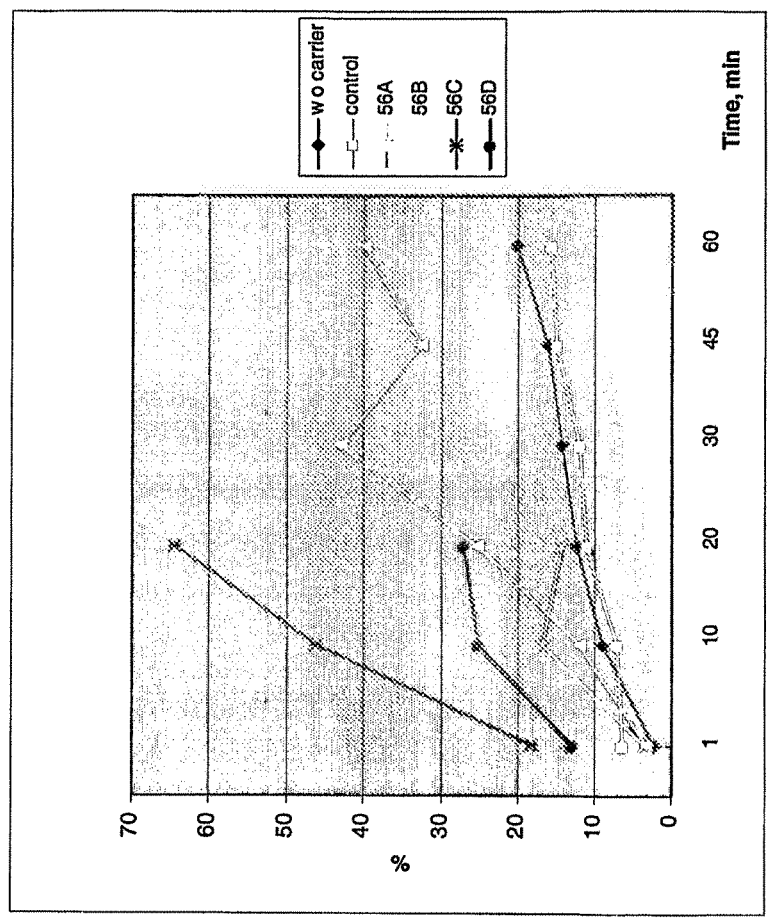
FIG. 7 is a line graph showing the percent of dead (red) Jurkat cells following exposure to the MVC/HT/56 A, B, C and D films of the present invention.
Figure 8B:
FIGS. 8A-D are photomicrographs illustrating the cytotoxic effect of BIOACT 13, 15, 16 and 110 films on Jurkat cells using LIVE/DEAD® BacLight™ Bacterial Viability Kit (Molecular probes) in which dead cells appear red and live cells appear green under a fluorescent microscope.
Figure 8D:
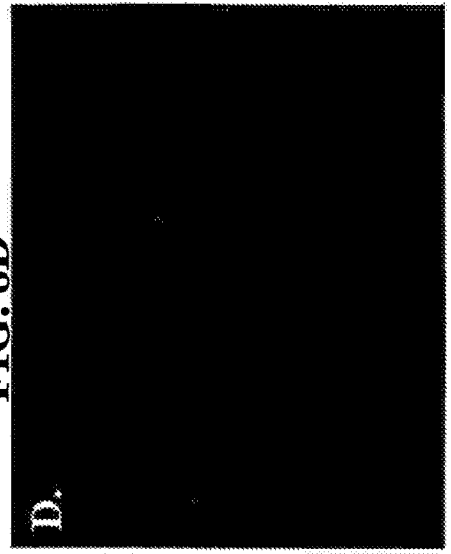
Figure 8A:
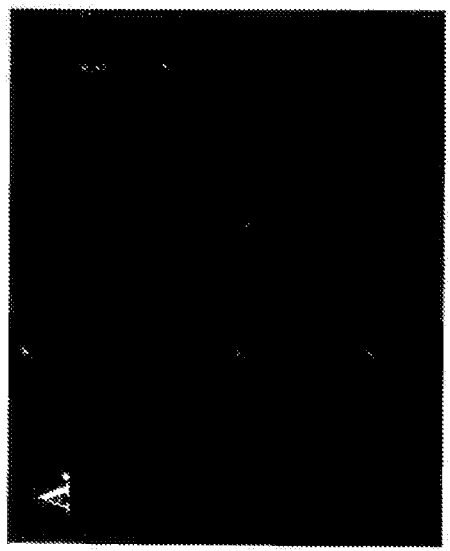
Figure 8C:
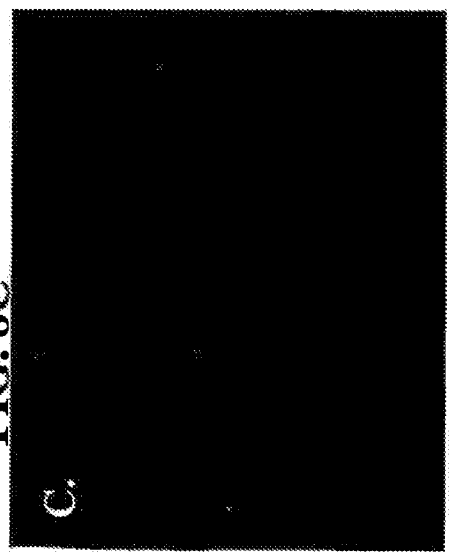
Figure 9B:
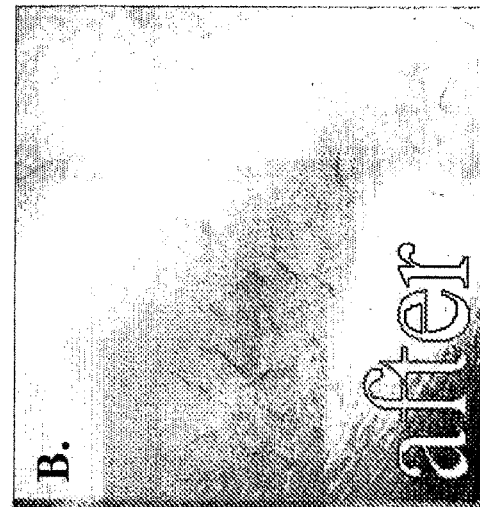
FIGS. 9A-C are photographs illustrating the anti-necrotic effect of ion exchange resin beads.
Figure 9A:
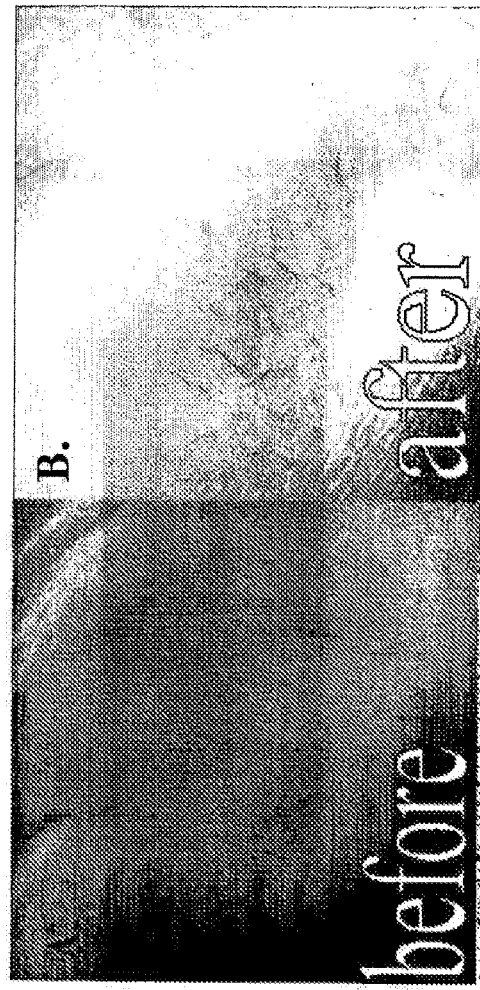
Figure 9C:

Cytotoxic activity testing of MVC HT 56A, B, C and D: As can be seen from FIG. 7 and Table 4 herein below interaction of Jurkat cells with 56/A and 56/C films differs from 56/B and 56/D.

TABLE 4

| | Time, min | | | | | |
|---|---|---|---|---|---|---|
| | 1 | 10 | 20 | 30 | 45 | 60 |
| | | | % of dead Jurkat cells | | | |
| wo carrier | 2.3 | 8.9 | 12.6 | 14.4 | 16.3 | 20.2 |
| control | 6.3 | 7.1 | 11 | 12 | 15 | 15.7 |
| 56A | 3.2 | 12 | 25.4 | 43.1 | 32.8 | 40 |
| 56B | 3.5 | 17 | 14.4 | | | |
| 56C | 18.5 | 46.1 | 64.6 | | | |
| 56D | 13 | 25.3 | 27 | | | |

Antibacterial activity testing of BIOACT 13, 15 and 16: Following 45 minutes of incubation on BIOACT 13, 50-70% of *E. coli* cells were dead. At the same time, 20-40% of *E. coli* were dead following incubation on BIOACT 15. *E. coli* cells were not attached to BIOACT 16. Following 20-30 minutes of incubation on BIOACT 15, almost all *E. coli* cells were dead. Evaluation of the attachment of these cells was difficult due to a high background noise level.

Cytotoxic activity testing of BIOACT 13, 15 and 16: The results from 3 separate experiments are illustrated below in Table 5 and are presented as the number of green:red Jurkat cells and percentage of green overall.

TABLE 5

| | Ex. 1 (1 minute) | Ex. 2 (1 minute) | Ex. 3 (1 minute) | Ex. 1 (10 minutes) | Ex. 2 (10 minutes) | Ex. 3 (10 minutes) |
|---|---|---|---|---|---|---|
| wo carrier | 81/13 (13.8) | 288/8 (2.7) | 308/9 (2.8) | 120/20 (14.3) | 300/29 (8.8) | 260/21 (7.5) |
| 13 | 250/15 (5.7) | 400/26 (6.1) | 360/26 (6.7) | 28/14 (33.3) | 80% | 60% |
| 15 | 160/14 (8.1) | 280/12 (4.1) | 280/8 (2.8) | 200/160 (44.4) | 81/5 (6.2) | 160/40 (20) |
| 16 | 120/13 (9.8) | 320/7 (2.1) | 376/29 (7.2) | 144/25 (14.8) | 100/6 (5.7) | 364/30 (7.6) |
| 110 | 100/5 (4.8) | 250/6 (2.3) | 320/13 (3.9) | 23/58 (71.6) | 216/15 (6.5) | 66/28 (29.5) |

Table 6 hereinbelow summarizes the results from the three experiments as the percentage of red cells. FIGS. 8A-D illustrate a typical experiment following exposure of Jurkat cells to Bioact 13

TABLE 6

| | 1 minute | 10 minute |
|---|---|---|
| wo carrier | 6.4 | 10.2 |
| 13 | 6.2 | 57.8 |
| 15 | 5 | 23.5 |
| 16 | 6.4 | 9.4 |
| 110 | 3.7 | 35.9 |

Conclusion

Interaction of *E. coli* cells and Jurkat cells with 56/A and 56/C films differs from 56/B and 56/D. In the BIOACT 13, 15 and 16 series, BIOACT 13 showed the highest cytotoxic and anti-bacterial activity.

Example 12

Bactericidal Activity of Nafion and Polyacrylamide pH Gels

The following toxicity tests were performed to ascertain whether Nafion and other films are toxic to bacteria.

Materials and Methods

Six types of plastic films were tested for bactericidal effects:

1. Nafion (commercial, Dupont);
2. Nafion (commercial, Dupont);
3. 500 micron thick polyacrylamide with immobilines on polyester base pH 10;
4. Same as 3 at pH 9;
5. Polyuretane film (commercial);
6. 500 micron poyacrylamide on polyester pH 5; Control- polyester film Testing Staph. Aureus, Staph. Spp, Strept. Beta-hemolit-gr.A and Strept. Beta-hemolitgr.G: The viability of these bacteria was tested on blood agar using the "sow" method. Essentially, 0.01 ml of microbial liquid culture was spread on blood agar using a special bacterial loop. Each of the six plastic films (10 mm×10 mm) was placed on the testing plate with active side down. Following overnight incubation at 37° C., the number of colonies was evaluated. The test and control groups were compared.

Testing total microbial and fungal agents: The total antimicrobial and anti-fungal effect of the above films was tested on Saburo agar using the "sedimentation" method. Uncovered plates with Saburo agar were placed for 8 hours in the open. Each of the six plastic films (10 mm×10 mm) was placed on the testing plate with active side down. Following overnight incubation at 37° C., the number of colonies was evaluated. The test and control groups were compared.

Results

The effects of the sheets of the present invention on *Staphaureus* growth are summarized in Table 7. The effects of the sheets of the present invention on *Staph.* Spp growth are summarized in Table 8. The effects of the sheets of the present invention on Strept. Beta-hemolit.gr.A growth are summarized in Table 9. The effects of the sheets of the present invention on Strept. Beta-hemolit.gr.G growth are summarized in Table 10. The effects of the sheets of the present invention on total microbial and fungi agents are summarized in Table 11.

TABLE 7

| sheet | *Staph. aureus* growth (agents/ml) | Control (agents/ml) |
|---|---|---|
| 1 | $2*10^3$ | $>10^6$ |
| 2 | $<10^3$ | $>10^6$ |
| 3 | $<10^3$ | $>10^6$ |
| 4 | $4.5*10^4$ | $>10^6$ |
| 5 | $9.9*10^4$ | $>10^6$ |
| 6 | $7.36*10^5$ | $>10^6$ |

TABLE 8

| sheet | *Staph.* Spp (agents/ml) | Control (agents/ml) |
|---|---|---|
| 1 | $<10^3$ | $>10^6$ |
| 2 | $<10^3$ | $>10^6$ |
| 3 | $9*10^3$ | $>10^6$ |
| 4 | $2.7*10^4$ | $>10^6$ |
| 5 | $4.29*10^5$ | $>10^6$ |
| 6 | $8.03*10^5$ | $>10^6$ |

TABLE 9

| sheet | *Strept* betta-hemolit. gr. A (agents/ml) | Control (agents/ml) |
|---|---|---|
| 1 | $3*10^3$ | $>10^6$ |
| 2 | $<10^3$ | $>10^6$ |
| 3 | $<10^3$ | $>10^6$ |
| 4 | $1.1*10^4$ | $>10^6$ |
| 5 | $6.71*10^5$ | $>10^6$ |
| 6 | $8.59*10^5$ | $>10^6$ |

TABLE 10

| sheet | *Strept* betta-hemolit. gr. G (agents/ml) | Control (agents/ml) |
|---|---|---|
| 1 | $2*10^3$ | $>10^6$ |
| 2 | $5*10^3$ | $>10^6$ |
| 3 | $4*10^3$ | $>10^6$ |
| 4 | $2.1*10^4$ | $>10^6$ |
| 5 | $8.61*10^5$ | $>10^6$ |
| 6 | $7.8*10^5$ | $>10^6$ |

TABLE 11

| sheet | Total microbial and fungi agents (colonies) | Control (colonies) |
|---|---|---|
| 1 | 3 | 22 |
| 2 | 2 | 18 |
| 3 | 1 | 17 |
| 4 | 9 | 19 |
| 5 | 19 | 21 |
| 6 | 19 | 19 |

Conclusion

Both Nafion and sheet no. 3 (the 500 micron thick polyacrylamide with immobilines on polyester base pH 10) showed high antibacterial activities and total antimicrobial and antifungal activities.

Example 13

Shelf Life Tests on Milk

The films of the present invention were tested for their effect on milk shelf life.

Materials and Methods

Pasteurized, homogenized milk was used in order to test milk stability with the films of the present invention. In both sets of experiments the milk was UV treated.

Test 1: Seven empty 35 mm Petri plates were filled to the top with fresh milk. Six plates were covered with the films of the present invention, so that their active side contacted the milk w/o air between them. The seventh plate was used as a control. Plates were placed on the table at room temperature for six days. Each day the pH of the plate was tested. In order to compensate for evaporation, sterile DDW was added each day. The total volume of added DDW was less then 5% of the total milk volume and therefore was not expected to influence pH dynamics. This experiment was repeated twice.

Test 2-14 day test with Nafion: This test was performed with commercial Nafion as the active material (layer). Pasteurized, homogenized milk (w/o antibiotics) was used in order to test milk stability. Three empty 35 mm Petri plates were filled with fresh milk up to the top. Two were covered with Nafion, so that active side contacted the milk w/o air between them. The third plate was used as control. Plates were placed on the table at room temperature for fourteen day. Each day pH of the plate was tested. In order to compensate for evaporation, sterile DDW was added each day. The total volume of added DDW was less then 5% of the total milk volume and therefore was not expected to influence pH dynamics.

Testing total microbial and fungal agents: This was tested on Saburo agar using the "sedimentation" method. Uncovered plates with Saburo agar were placed for 8 hours in the open. A piece of Nafion (10 mm×10 mm) was placed on the testing plate with active side down. Following overnight incubation at 37° C., the number of colonies was evaluated. Test and control groups were compared.

Results

The pH results of the milk following test 1 are recorded in Table 12 hereinbelow.

TABLE 12

| | 1 day | 2 day | 3 day | 4 day | 5 day | 6 day |
|---|---|---|---|---|---|---|
| Film 1 | 7.4 | 7.2 | 6.9 | 6.8 | 6.7 | 6.3 |
| Film 2 | 7.4 | 7.3 | 6.8 | 6.6 | 6.2 | 6.1 |
| Film 3 | 7.4 | 7.3 | 6.9 | 5.9 | 5.4 | 4.9 |
| Film 4 | 7.4 | 7.0 | 6.6 | 6.1 | 5.5 | 4.7 |
| Film 5 | 7.4 | 6.8 | 6.2 | 5.6 | 4.4 | 3.7 |
| Film 6. | 7.4 | 7.0 | 6.6 | 5.6 | 4.8 | 4.1 |
| Control | 7.4 | 6.9 | 6.1 | 5.4 | 4.1 | 4.0 |

The pH results of the milk (test 1, repeat experiment) are recorded in Table 13 hereinbelow.

TABLE 13

| Day | pH |
|---|---|
| Day 0 | 8.5 |
| Day 1 | 8.7 |
| Day 2 | 8.8 |
| Day 3 | 8.7 |
| Day 4 | 8.5 |
| Day 5 | 8.6 |
| Day 6 | 8.9 |
| Day 7 | 8.5 |
| Day 8 | 8.3 |
| Day 9 | 8.5 |

TABLE 13-continued

| Day | pH |
|---|---|
| Day 10 | 8.7 |
| Day 11 | 8.8 |
| Day 12 | 8.5 |
| Day 13 | 8.5 |
| Day 14 | 8.4 |
| Day 15 | 8.5 |

The pH results of the 14 day test (test 2) are recorded in Table 14 hereinbelow.

TABLE 14

| | 1 day | 2 day | 3 day | 4 day | 5 day | 6 day | 7 day |
|---|---|---|---|---|---|---|---|
| Nafion 1 | 7.5 | 7.4 | 7.3 | 7.1 | 7.1 | 7 | 6.8 |
| Nafion 2 | 6.8 | 6.6 | 6.6 | 6.7 | 6.6 | 6.5 | 6.5 |
| Control | 7.4 | 6.7 | 6.2 | 5.1 | 4.2 | 4.1 | 4.1 |

| | 8 day | 9 day | 10 day | 11 day | 12 day | 13 day | 14 day |
|---|---|---|---|---|---|---|---|
| Nafion 1 | 6.8 | 6.6 | 6.6 | 6.7 | 6.6 | 6.5 | 6.5 |
| Nafion 2 | 4.7 | 4.6 | 4.4 | 4.5 | 4.4 | 4.4 | 4.3 |
| Control | 4.2 | 4.2 | 4.1 | 4.1 | 4.2 | 4.1 | 4.1 |

The results from testing total microbial and fungal agents are recorded in Table 15 hereinbelow.

TABLE 15

| | Total microbial and fungi agents (colonies) | | |
|---|---|---|---|
| No | First | Second | Control (colonies) |
| 1 | 2 | 1 | 14 |
| 2 | 2 | 2 | 31 |
| 3 | 3 | 3 | 24 |
| 4 | 0 | 6 | 25 |
| 5 | 4 | 5 | 16 |
| 6 | 0 | 2 | 20 |
| 7 | 2 | 5 | 19 |
| 8 | 3 | 2 | 13 |
| 9 | 2 | 2 | 37 |
| 10 | 1 | 3 | 25 |

Example 14

Cytotoxicity Testing of Second Series of Laminates

A second series of polyester base laminates were prepared by thermoplastic lamination methods. The laminates consisted of active anionic components in a PVOH matrix. In some samples the active layer was over-coated with a layer of PVOH.

The compositions and structure of laminates are provided in Table 16 hereinbelow.

TABLE 16

| Coating | Coating Formulation (PVOH + Active Component) | T(gsm) | Ratio | $T_1(\mu)$ | $T_2(\mu)$ |
|---|---|---|---|---|---|
| 1 | PVOH + p Toluene sulphonic acid salt of Poly (Dimethylamineethylmethacrylate) | 0.9 | 3/2 | 18 | 0 |
| 2 | PVOH + p Toluene sulphonic acid salt of Poly (Dimethylamineethylmethacrylate) | 1.8 | 3/2 | 9 | 0 |
| 3 | PVOH + p Toluene sulphonic acid salt of Poly (Dimethylamineethylmethacrylate) | 0.9 | 3/2 | 9 | 24 |
| 4 | PVOH + p Toluene sulphonic acid salt of Poly (Dimethylamineethylmethacrylate) | 0.9 | 3/2 | 9 | 100 |
| 5 | PVOH + p Toluene sulphonic acid salt of Poly (Dimethylamineethylmethacrylate) | 0.9 | 3/2 | 9 | 0 |

TABLE 16-continued

| Coating | Coating Formulation (PVOH + Active Component) | T(gsm) | Ratio | $T_1(\mu)$ | $T_2(\mu)$ |
|---|---|---|---|---|---|
| 6 | PVOH + p Toluene sulphonic acid salt of Poly (Dimethylamineethylmethacrylate) | 1.8 | 3/2 | 18 | 0 |
| 7 | PVOH + p Toluene sulphonic acid salt of Poly (Dimethylamineethylmethacrylate) | 0.9 | 3/2 | 9 | 24 |
| 8 | As above + Laponite | 0.58 | 4/1 | 6 | 0 |

(T-total thickness in gram/square meter; R- ratio of the active component and the PVOH binder; $T_1$ - approximate thickness in microns, $T_2$ - thickness in microns of the overlay PVOH layer).

Materials and Methods

Determination of pH: Following wetting of the films in water, pH was determined using pH-Fix 0-14 (Macherey-Nagel).

Cytotoxicity testing: Cytotoxicity tests were performed as described in Examples 12 and 13.

Results

The pH results are set forth in Table 17 hereinbelow.

TABLE 17

| Film | pH |
|---|---|
| 1. MVC/HT/58/AY | 5.0 |
| 2. MVC/HT/58/AY - pH 5.0 | 5.0 |
| 3. MVC/HT/58/AYTCG - pH 6.0 | 6.0 |
| 4. MVC/HT/58/AYTCG - pH 6.0 | 6.0 |
| 5. MVC/HT/58/BY | <5.0 (4.8) |
| 6. MVC/HT/58/BR | 4.0 |
| 7. MVC/HT/58/BYTCG | <5.0 (4.8) |
| 8. MVC/HT/58/CY | 6.0 |

The cytotoxicity results are set forth in Table 18 hereinbelow. Cytotoxic effect was measured as the % of PI-stained (dead) cells. Following 20 minutes, approximately 80% of cells were green in Control sample (without film).

TABLE 18

| No. | Designation | Cytotoxic effect, % | | | |
|---|---|---|---|---|---|
| | | 1 min | 2 min | 10 min | 20 min |
| 1 | AY | 95 | ND | 100 | ND |
| 2 | AR | 85 | ND | 100 | ND |
| 3 | AYTCG | 95 | ND | 100 | ND |
| 4 | AYTCB | 50* | 90 | 100 | ND |
| 5 | BY | 90 | ND | 100 | ND |
| 6 | BR | 70* | ND | 100* | ND |
| 7 | BYTCG | 5 | ND | 100* | 100 |
| 8 | CY | 10* | ND | 50* | 50* |

Of note, samples 3, 4 and 7 have a neutral PVOH overcoat and still demonstrated high cytotoxicity.

We claim:

1. A solid buffer comprising one or more solid ion exchange materials having one or more functional groups selected to dissociate H+ions, wherein said solid buffer having volumetric buffering capacity greater than about 20 mM H+/(L.pH unit) in an environment capable of transporting H+ions, said solid buffer comprises a sulfonated polystyrene polymer or a sulfonated tetrafluoroethylene copolymer and is adapted to cause the death of at least one target cell within or in contact with said environment.

2. The solid buffer of claim 1 wherein said target cell is a bacterial cell, a fungal cell or a yeast cell.

3. The solid buffer of claim 2 wherein said target cell is a bacterial cell.

4. The solid buffer of claim 1 wherein said solid buffer is adapted to kill said target cell without inserting any of its structure into the membrane of said target cell.

5. The solid buffer of claim 1 wherein the volumetric buffering capacity is at least about 50 mM H$^+$/(L·pH unit).

6. The solid buffer of claim 1 wherein the volumetric buffering capacity is at least about 100 mM H$^+$/(L·pH unit).

7. The solid buffer of claim 1 wherein the H+ concentration is greater than about $3.2 = 10^{-5}$ M or less than about $10^{-8}$ M.

8. The solid buffer of claim 1 wherein the solid buffer comprises a pH gradient along at least a portion thereof.

9. The solid buffer of claim 1 wherein the solid buffer comprises a plurality of regions of differing pH.

10. The solid buffer of claim 1 wherein the ion exchange material is a polymer.

11. The solid buffer of claim 1 wherein the solid buffer comprises one or more of an ion exchange bead, a polymer-coated ion exchange bead, and an ion exchange material incorporated in a matrix.

12. The solid buffer of claim 1 wherein the solid buffer comprises at least a portion of a coating or a component of a medical device, a wound dressing, sutures, cloth, fabric and a wound ointment.

13. The solid buffer of claim 1 wherein the solid buffer is in the form of a shaped article, a coating, a spray, a film, a laminate on a film, a film in a laminate, sheets, beads, beads incorporated in fabric, particles, microparticles, microcapsules, microemulsions or nanoparticles.

14. The solid buffer of claim 1 covered by a barrier layer, said barrier layer is selectively permeable to water.

15. The solid buffer of claim 1 covered by a barrier layer, said barrier layer is permeable to a preselected target cell but not to preselected non-target cells.

16. The solid buffer of claim 1 wherein the sulfonated polystyrene polymer is sulfonated polystyrene divinylbenzene.

* * * * *